US010610462B2

(12) United States Patent
Renn et al.

(10) Patent No.: US 10,610,462 B2
(45) Date of Patent: Apr. 7, 2020

(54) AQUEOUS DENTAL GLASS IONOMER COMPOSITION

(71) Applicant: DENTSPLY SIRONA Inc., York, PA (US)

(72) Inventors: Caroline Renn, Singen (DE); Oliver Elsner, Radolfzell (DE); Maximilian Maier, Constance (DE); Florian Szillat, Constance (DE); Joachim Klee, Radolfzell (DE); Christoph Weber, Constance (DE); Uwe Walz, Constance (DE); Christian Scheufler, Engen (DE); Helmut Ritter, Wuppertal (DE); Andrew Lichkus, York, PA (US); Xiaoming Jin, Middletown, DE (US)

(73) Assignee: DENTSPLY SIRONA INC., York, PA (US)

( * ) Notice: Subject to any disclaimer, the term of this patent is extended or adjusted under 35 U.S.C. 154(b) by 75 days.

(21) Appl. No.: 15/486,335

(22) Filed: Apr. 13, 2017

(65) Prior Publication Data
US 2017/0296441 A1    Oct. 19, 2017

Related U.S. Application Data

(60) Provisional application No. 62/322,983, filed on Apr. 15, 2016.

(51) Int. Cl.
*C08L 33/00* (2006.01)
*A61K 6/889* (2020.01)

(52) U.S. Cl.
CPC ................... *A61K 6/889* (2020.01)

(58) Field of Classification Search
None
See application file for complete search history.

(56) References Cited

U.S. PATENT DOCUMENTS

| | | | | |
|---|---|---|---|---|
| 3,655,605 A * | 4/1972 | Smith | ............. | A61K 6/0023 106/35 |
| 3,814,717 A * | 6/1974 | Wilson | ............. | A61K 6/0023 106/35 |
| 4,143,018 A * | 3/1979 | Crisp | ............. | A61K 6/0675 260/998.11 |
| 4,209,434 A * | 6/1980 | Wilson | ............. | A61K 6/0835 106/35 |
| 4,360,605 A * | 11/1982 | Schmitt | ............. | A61K 6/0835 433/228.1 |
| 4,376,835 A * | 3/1983 | Schmitt | ............. | A61K 6/0835 106/35 |
| 4,900,546 A * | 2/1990 | Posey-Dowty | ....... | A61L 24/001 514/29 |
| 5,130,347 A * | 7/1992 | Mitra | ............. | A61K 6/0017 433/228.1 |
| 2002/0010227 A1* | 1/2002 | Culbertson | ............. | A61K 6/083 523/115 |
| 2004/0157954 A1* | 8/2004 | Imai | ............. | A61L 24/06 523/115 |
| 2005/0252413 A1* | 11/2005 | Kangas | ............. | A61K 6/0017 106/35 |
| 2009/0105144 A1* | 4/2009 | Vogt | ............. | A61L 24/0094 514/8.2 |
| 2009/0105367 A1* | 4/2009 | Vogt | ............. | A61L 24/001 523/116 |
| 2009/0105369 A1* | 4/2009 | Vogt | ............. | A61L 24/001 523/116 |
| 2010/0228358 A1* | 9/2010 | Leonard | ............. | A61L 24/001 623/23.62 |
| 2010/0329074 A1* | 12/2010 | Vogt | ............. | A61B 17/8825 366/190 |
| 2013/0289216 A1* | 10/2013 | Klee | ............. | A61K 6/0835 525/285 |
| 2014/0228474 A1* | 8/2014 | Qian | ............. | A61K 6/0835 523/116 |
| 2018/0353391 A1* | 12/2018 | Renn | ............. | A61K 6/0835 |

FOREIGN PATENT DOCUMENTS

| | | |
|---|---|---|
| EP | 1911434 A1 | 4/2008 |
| WO | 03011232 A1 | 2/2003 |

(Continued)

OTHER PUBLICATIONS

2-Hydroxyethyl methacrylate OECD SIDS, p. 5, Aug. 22, 2001 (Year: 2001).*

(Continued)

*Primary Examiner* — Peter A Salamon
(74) *Attorney, Agent, or Firm* — Dentsply Sirona Inc.

(57) ABSTRACT

The present disclosure relates to an aqueous dental glass ionomer composition comprising a reactive particulate glass, a water-soluble, polymerizable polymer which is reactive with the particulate glass in a cement reaction, a hydrolysis-stable, water-soluble monomer having a single polymerizable double bond and optionally a carboxylic acid group or hydroxyl group; and a polymerization initiator system, wherein the polymerizable polymer is obtainable by a process comprising a step of polymerizing a mixture comprising a first polymerizable monomer comprising at least one optionally protected carboxylic acid group and a first polymerizable organic moiety, and optionally a second copolymerizable monomer comprising one or more optionally protected primary and/or secondary hydroxyl and/or amino group(s) and a second polymerizable organic moiety, for obtaining an water-soluble polymer; a step of coupling to the water-soluble polymer a compound having a polymerizable moiety and a functional group reactive with an optionally protected carboxylic acid group of repeating units derived from the first polymerizable monomer or an optionally protected hydroxyl and/or amino group of repeating units derived from the second copolymerizable monomer in the water-soluble polymer obtained in step a), wherein the optionally protected carboxylic acid group and the optionally protected hydroxyl and/or amine group are deprotected, so that polymerizable pendant groups are linked to the backbone by ester groups, urethane groups and/or amide groups, and, optionally, a step of deprotecting the protected carboxylic acid group for obtaining a polymerizable polymer.

15 Claims, No Drawings

(56) References Cited

FOREIGN PATENT DOCUMENTS

WO     WO-03011232 A1 *   2/2003   .......... A61K 6/0835
WO       2012084206 A1    6/2012

OTHER PUBLICATIONS

Acrylamide, International Program of Chemical Safety, EHC 49, 1985 (Year: 1985).*
European Search Report dated Sep. 13, 2017.

* cited by examiner

AQUEOUS DENTAL GLASS IONOMER COMPOSITION

FIELD OF THE INVENTION

The present disclosure relates to an aqueous dental glass ionomer composition and a process for the preparation thereof. Furthermore, the present disclosure relates to the use of a mixture comprising a specific water-soluble, polymerizable polymer comprising acidic groups and a specific hydrolysis stable, water-soluble monomer for the preparation of a dental composition.

The aqueous dental glass ionomer composition according to the present disclosure provides a cured glass ionomer composition having excellent mechanical properties and long-term mechanical resistance.

BACKGROUND

Dental restorative materials are used for restoring the function, morphology and integrity of dental structures damaged by physical damage or caries-related decay of enamel and/or dentin. Dental restorative materials are required to have high biocompatibility, good mechanical properties and mechanical resistance over a long period of time.

Dental restorative materials include glass ionomer cements having good biocompatibility and good adhesion to hard dental tissues. Moreover, glass ionomer cements may provide cariostatic properties through the release of fluoride ions. Glass ionomer cements are cured by an acid-base reaction between a reactive glass powder and a polyalkenoic acid. However, conventional glass ionomer cements have a relatively low flexural strength and are brittle due to salt-like structures between the polyacid and the basic glass.

The mechanical properties of glass ionomer cements may be improved by the selection of the polyacidic polymer. For example, a polymer having polymerizable moieties as pendant groups can be crosslinked in order to increase the mechanical resistance of the resulting glass ionomer cement.

WO 03/011232 A1 discloses glass ionomer cements containing two types of polymers, namely a first polymer having a plurality of acidic repeating units, but being substantially free of polymerizable vinyl groups, and a second polymer having a plurality of acidic repeating units and a plurality of polymerizable vinyl groups. The second polymer may be prepared by reacting a polymer having a plurality of carboxylic acid groups with the coupling agent isocyanatoethyl methacrylate, wherein the carboxylic acid groups react with the isocyanato group of the coupling agent, whereby an amide bond is formed. Thereby, the pendant polymerizable vinyl groups in the form of a methacrylate group are introduced.

WO 93/016676 A1 discloses water-based dental glass ionomer cements from ß-dicarbonyl polymers. The dental glass ionomer cements may contain a polymer comprising a) pendant ß-dicarbonyl groups, such as ß-diesters, ß-diketones or ß-ketoesters, capable of undergoing a setting reaction in the presence of water, and a reactive powder, b) crosslinkable groups capable of undergoing a free-radical or cationic crosslinking reaction, and c) optionally an ionic group, such as a carboxyl group, capable of undergoing a setting reaction in the presence of water and a reactive powder. For introducing the crosslinkable groups, a polymer containing pendant ß-dicarbonyl groups and pendant carboxyl groups is reacted with coupling compounds which comprise a polymerizable carbon-carbon double bond in the form of a (meth) acrylate or allyl group, and a group providing for attachment to the pendant carboxyl groups, namely a hydroxyl group, an amine group, an epoxide group or an isocyanate group.

SUMMARY

It is an object of the present disclosure to provide an aqueous dental glass ionomer composition providing improved mechanical properties including high biaxial flexural strength and providing a clinically relevant adhesion to tooth structure after curing, as well as hydrolysis-stability in an aqueous medium before and after curing, in particular in an acidic medium.

According to a first aspect, the present disclosure provides an aqueous dental glass ionomer composition comprising
(A) a reactive particulate glass,
(B) a water-soluble, polymerizable polymer comprising acidic groups, which is reactive with the particulate glass in a cement reaction, whereby the polymerizable polymer has a polymer backbone and pendant groups having one or more polymerizable carbon-carbon double bonds, wherein the polymerizable polymer is obtainable by a process comprising
  a) a step of polymerizing a mixture comprising
    (i) a first polymerizable monomer comprising at least one optionally protected carboxylic acid group and a first polymerizable organic moiety, and optionally
    (ii) a second copolymerizable monomer comprising one or more optionally protected primary and/or secondary hydroxyl and/or amino group(s) and a second polymerizable organic moiety, for obtaining an water-soluble polymer;
  b) a step of coupling to the water-soluble polymer a compound having a polymerizable moiety and a functional group reactive with an optionally protected carboxylic acid group of repeating units derived from the first polymerizable monomer or an optionally protected hydroxyl and/or amino group of repeating units derived from the second copolymerizable monomer in the water-soluble polymer obtained in step a), wherein the optionally protected carboxylic acid group and the optionally protected hydroxyl and/or amino group are deprotected, so that polymerizable pendant groups are linked to the backbone by ester groups, urethane groups and/or amide groups, and optionally,
  a step of deprotecting the protected carboxylic acid group after step a) or step b), for obtaining a polymerizable polymer;
(C) a hydrolysis-stable, water-soluble monomer having a single polymerizable double bond and optionally a carboxylic acid group or hydroxyl group; and
(D) a polymerization initiator system.

Specifically, in the coupling step b), the polymerizable pendant groups are linked to the backbone by ester groups, urethane groups and/or amide groups.

According to a second aspect, the present disclosure provides a use of a mixture comprising an aqueous dental glass ionomer composition comprising
(B) a water-soluble, polymerizable polymer comprising acidic groups, which is reactive with the particulate glass in a cement reaction, whereby the polymerizable polymer has a polymer backbone and pendant groups having one or more polymerizable carbon-carbon double bonds, wherein the polymerizable polymer is obtainable by a process comprising a) a step of polymerizing a mixture comprising
  (i) a first polymerizable monomer comprising at least one optionally protected carboxylic acid group and a first polymerizable organic moiety, and
  (ii) optionally copolymerizing a second copolymerizable monomer comprising one or more optionally protected primary and/or secondary hydroxyl and/or amino group(s) and a second polymerizable organic moiety,
  for obtaining an water-soluble polymer;
b) a step of coupling to the water-soluble polymer a compound having a polymerizable moiety and a functional group reactive with an optionally protected carboxylic acid group of repeating units derived from the first polymerizable monomer or an optionally protected hydroxyl and/or amino group of repeating units derived from the second copolymerizable monomer in the water-soluble polymer obtained in step a), wherein the optionally protected carboxylic acid group and the optionally protected hydroxyl and/or amino group are deprotected, so that polymerizable pendant groups are linked to the backbone by ester groups, urethane groups and/or amide groups,
  and, optionally, a step of deprotecting the protected carboxylic acid group after step a) or step b), for obtaining a polymerizable polymer; and s
(C) a hydrolysis-stable, water-soluble monomer having a single polymerizable double bond and optionally a carboxylic acid group or hydroxyl group;
for the preparation of a dental composition, in particular a dental composition according to the first aspect.

According to a third aspect, the present disclosure provides a process for the preparation an aqueous dental glass ionomer composition according to the first aspect, which comprises
a) a step of polymerizing a mixture comprising
  (i) a first polymerizable monomer comprising at least one optionally protected carboxylic acid group and a first polymerizable organic moiety, and optionally
  (ii) a second copolymerizable monomer comprising one or more optionally protected primary and/or secondary hydroxyl and/or amino group(s) and a second polymerizable organic moiety,
  for obtaining an water-soluble polymer;
b) a step of coupling to the water-soluble polymer a compound having a polymerizable moiety and a functional group reactive with an optionally protected carboxylic acid group of repeating units derived from the first polymerizable monomer or an optionally protected hydroxyl and/or amino group of repeating units derived from the second copolymerizable monomer in the water-soluble polymer obtained in step a), wherein the optionally protected carboxylic acid group and the optionally protected hydroxyl and/or amino group are deprotected, so that polymerizable pendant groups are linked to the backbone by ester groups, urethane groups and/or amide groups,
  and, optionally, a step of deprotecting the protected carboxylic acid group after step a) or step b), for obtaining a polymerizable polymer.

A cured aqueous dental glass ionomer composition according to the present disclosure has excellent mechanical properties based on the specific combination of the polymerizable polymer according to (B) and the monomer having a single polymerizable double bond according to (C). After polymerization of the polymerizable polymer according to (B) and the monomer having a single polymerizable double bond according to (C), the polymer may contain an increased number of acidic groups when the monomer having a single polymerizable double bond according to (C) contains a carboxylic acid group. Furthermore, the polymer may contain additional hydroxyl groups when the monomer having a single polymerizable double bond according to (C) contains a hydroxyl group. Accordingly, crosslinking by a cement reaction and adhesion to dental hard tissue may be improved.

The inventors have recognized that resin reinforced dental glass ionomer cements are subject to deterioration during storage or after curing in the mouth of the patient. The inventors have further recognized that the deterioration includes hydrolytic degradation of the resin component conventionally containing hydrolyzable moieties. The inventors have then recognized that by using a specific process for the preparation of a polymer, an improved water-soluble, polymerizable polymer according to (B) may be prepared at a high molecular weight which overcomes the drawbacks of conventional resin reinforced glass ionomer cements known from the prior art. In said polymerizable polymer according to (B), the introduction of carboxylic acid group and optionally hydroxyl group containing repeating units into the backbone of the polymer allows to provide high molecular weight copolymers having polymerizable pendant groups linked to the backbone by ester or urethane linking groups. Thereby, the disadvantages of conventional polymerizable resin components may be avoided.

The polymerizable pendant groups of the polymerizable polymer according to (B) may react with the monomer having a single polymerizable double bond according to (C), whereby a polymer network is formed. The grafted sidechains may contain additional carboxylic acid or hydroxyl groups which can take part in a cement reaction, thereby further increasing the strength of the cured composition.

A crosslinked polymer may be obtained by optional crosslinker(s), which crosslink polymerizable polymers according to (B).

DETAILED DESCRIPTION

In the following, sometimes components (A), (B), (C) and (D) of the present aqueous dental glass ionomer composition are referred to by the terms "(reactive particulate) glass according to (A)", "(water-soluble) polymerizable polymer (comprising acid groups) according to (B)", "(hydrolysis-stable, water-soluble) monomer (having a single polymerizable double bond) according to (C)" and "polymerization initiator system according to (D)" respectively.

The term "(co)polymerizable" as used with the terms "first polymerizable monomer" having a "first polymerizable organic moiety", "second copolymerizable monomer" having a "second polymerizable organic moiety", "compound having a polymerizable moiety" having "polymerizable pendant groups", and the crosslinker as well as the hydrolysis-stable, water-soluble (meth)acrylamide) monomer having "a single polymerizable double bond" respectively mean compounds capable of combining by covalent bonding in an addition polymerization to form a polymer. Said "polymerizable polymer" may be combined with a crosslinker as well as with the hydrolysis-stable, water-soluble monomer having "a single polymerizable double bond" respectively to form graft polymers and/or crosslinked polymers when curing the aqueous dental glass ionomer composition.

The terms "first polymerizable organic moiety", "second polymerizable organic moiety", "polymerizable pendant groups" and "one polymerizable double bond" as used herein in connection components (B), (C) and the crosslinker (F) of the present aqueous dental glass ionomer composition mean any double bond capable of addition polymerization, in particular free radical polymerization, such as a carbon-carbon double bond.

The term "curing" means the polymerization of functional oligomers and monomers, or even polymers, into a polymer network. Curing is the polymerization of unsaturated monomers or oligomers in the presence of crosslinking agents.

The term "curable" refers to a aqueous dental glass ionomer composition that will polymerize into a crosslinked polymer network when irradiated for example with actinic radiation such as ultraviolet (UV), visible, or infrared radiation, or when reacted with polymerisation initiators.

The present aqueous dental glass ionomer composition provides a cured dental g lass-ionomer composition/cement. Said cured dental glass ionomer composition/cement is formed based on a reaction between (A) the reactive particulate glass, the above described components polymerizable polymer according to (B), monomer according to (C) and polymerization initiator system according to (D) in a cement reaction and a polyaddition reaction.

(A) The Reactive Particulate Glass

The aqueous dental glass ionomer composition according to the present disclosure comprises a reactive particulate glass. A reactive particulate glass is obtainable by transforming a solid mixture of metal oxides by a thermal melt process into a glass followed by milling, which glass is capable of reacting with a polymer containing acidic groups in a cement reaction. The glass is in a particulate form. Moreover, the reactive particulate glass may be surface modified, e.g. by silanation or acid treatment. Any conventional reactive dental glass may be used for the purpose of the present disclosure. Specific examples of particulate reactive glasses are selected from calcium alumino silicate glass, calcium alumino fluorosilicate glass, calcium aluminumfluoroborosilicate glass, strontium aluminosilicate glass, strontium aluminofluorosilicate glass, strontium aluminofluoroborosilicate glass. Suitable particulate reactive glasses may be in the form of metal oxides such as zinc oxide and/or magnesium oxide, and/or in the form of ion-leachable glasses, e.g., as described in U.S. Pat. Nos. 3,655,605, 3,814,717, 4,143,018, 4,209,434, 4,360,605 and 4,376,835.

In embodiments, the reactive particulate glass according to (A) is a reactive particulate glass comprising:
1) 20 to 45% by weight of silica,
2) 20 to 40% by weight of alumina,
3) 20 to 40% by weight of strontium oxide,
4) 1 to 10% by weight of $P_2O_5$, and
5) 3 to 25% by weight of fluoride.

The present aqueous dental glass ionomer composition comprises 20 to 90 percent by weight of the reactive particulate glass, such as 30 to 85 percent by weight based on the total weight of the composition or 20 to 80 percent by weight based on the total weight of the composition.

The reactive particulate glass usually has an average particle size of from 0.1 to 100 µm, such as from 1 to 40 µm as measured, for example, by electron microscopy or by using a conventional laser diffraction particle sizing method as embodied by a MALVERN Mastersizer S or MALVERN Mastersizer 2000 apparatus.

The reactive particulate glass may have a unimodal or multimodal (e.g., bimodal) particle size distribution, wherein a multimodal reactive particulate glass represents a mixture of two or more particulate fractions having different average particle sizes.

The reactive particulate glass may be a an agglomerated reactive particulate glass which is obtainable by agglomerating a reactive particulate glass in the presence of a modified polyacid and/or polymerizable (meth)acrylate resins. The particle size of the agglomerated reactive particulate glass may be adjusted by suitable size-reduction processes such as milling.

The reactive particulate glass may be surface modified by a component according to (B), (C) and/or (D). In particular, the reactive particulate glass may be surface modified by one or more components of the polymerization initiator system (D) in order to avoid contact of the one or more components of the polymerization initiator system (D) with an acid under aqueous conditions.

The reactive particulate glass may alternatively or additionally be surface modified by a surface modifying agent. The surface modifying agent may be a silane. A silane provides a suitable hydrophobicity to the reactive particulate glass, which allows for an advantageous, homogeneous admixture with the organic components according to (B), (C) and (D) of the aqueous dental glass ionomer composition.

(B) The Water-Soluble, Polymerizable Polymer Comprising Acidic Groups

The aqueous dental glass ionomer composition according to the present disclosure comprises a specific water-soluble, polymerizable polymer comprising acidic groups, which is reactive with the particulate glass in a cement reaction, The water-soluble, polymerizable polymer comprising acidic groups is an organic polymeric compound comprising ionizable pendant groups, such as carboxylic acid groups. The carboxylic acid groups of the polymer are capable of reacting with a reactive particulate glass in a cement reaction to form a glass ionomer cement.

The water-soluble, polymerizable polymer comprising acidic groups according to (B) is obtainable by a process comprising the polymerisation or copolymerization step a), the coupling step b), and an optional deprotection step.

The term "polymerizable polymer" used in connection with item (B) means a polymer containing one or more polymerizable moieties capable of polymerizing and crosslinking of the polymer for improving the mechanical properties and the long-term mechanical and chemical resistance of the cured aqueous dental glass ionomer composition.

The term "water-soluble" used in connection with the terms "(polymerizable) polymer" according to (B) and monomer according to (C) means that at least 0.1 g, such as 0.5 g of the polymerizable polymer or monomer dissolves in 100 g of water at 20° C.

The water-soluble, polymerizable polymer comprising acidic groups according to (B) is obtainable by a process comprising the (co)polymerizing step a) and the coupling step b).

Specifically, step a) represents a step of (co)polymerizing a mixture comprising (i) a first polymerizable monomer comprising at least one optionally protected carboxylic acid group and a first polymerizable organic moiety and optionally (ii) a second copolymerizable monomer comprising one or more optionally protected primary and/or secondary hydroxyl and/or amino group(s) and a second polymerizable organic moiety for obtaining a water-soluble polymer.

According to the present disclosure, one or a mixture of two or more monomers according to (i) and/or (ii) may be used in the (co)polymerizing step a).

Step b) represents a step of coupling to the water-soluble polymer obtained in step a) a compound having a polymerizable moiety and a functional group reactive with an optionally protected carboxylic acid group of repeating units derived from the first polymerizable monomer or an optionally protected hydroxyl and/or amino group of repeating units derived from the second copolymerizable monomer in the water-soluble polymer obtained in step a), wherein the optionally protected carboxylic acid group and the optionally protected hydroxyl and/or amino group are deprotected, so that polymerizable pendant groups are linked to the backbone by ester groups, urethane groups and/or amide groups, and optionally, a step of deprotecting the protected carboxylic acid group after step a) or step b), for obtaining a polymerizable polymer.

According to the present disclosure, one or a mixture of two or more compound(s) having a polymerizable moiety and a functional group reactive with an optionally protected carboxylic acid group of repeating units derived from the first polymerizable monomer or an optionally protected hydroxyl and/or amino group of repeating units derived from the second copolymerizable monomer may be used in the coupling step b).

The first polymerizable monomer to be used in step a) comprises at least one, such as one to three, one or two, or one optionally protected carboxylic acid group(s).

The protecting group of an optionally protected carboxylic acid group is not particularly limited as long as it is a carboxyl-protecting group known to those of ordinary skill in the art of organic chemistry (cf. P. G. M. Wuts and T. W. Greene, Greene's Protective Groups in Organic Synthesis, 4th Edition, John Wiley and Sons Inc., 2007). The carboxyl-protecting group may be selected from a trialkylsilyl group, an alkyl group and an arylalkyl group. The carboxyl-protecting group may be selected from an alkyl group or an arylalkyl group. The carboxyl-protecting group may further be selected from a tert-butyl group and a benzyl group. In one embodiment, the carboxyl-protecting group is a tert-butyl group.

The term "polymerizable organic moiety" as used herein means an organic moiety of a molecule which can be used to covalently link this molecule in a chemical reaction (polymerization) to other molecules reactive with this moiety to form a macromolecule of repeating or alternating structural units. This polymerizable organic moiety may be a carbon-carbon double bond as in the case of an ethylenically unsaturated moiety.

In one embodiment of the aqueous dental glass ionomer composition of the present disclosure, the first polymerizable monomer is represented by the general formula (1):

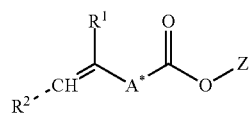

(1)

In formula (1), $R^1$ is a hydrogen atom, a —COOZ group, a linear $C_{1-6}$ or branched or cyclic $C_{3-8}$ alkyl group which may be substituted with a —COOZ group, or a $C_{6-10}$ aryl group which may be substituted with a —COOZ group. $R^1$ may be a hydrogen atom, a —COOZ group or a methyl group, or $R^1$ may be a hydrogen atom or a methyl group.

For $R^1$, a $C_{6-10}$ aryl group may, for example, be a phenyl group or a naphthyl group.

In formula (1), $R^2$ is a hydrogen atom, a —COOZ group, or a linear $C_{1-6}$ or branched or cyclic $C_{3-8}$ alkyl group which may be substituted with a —COOZ group. $R^2$ may be a hydrogen atom or a —COOZ group, or $R^2$ may be a hydrogen atom. In formula (1), the dotted line indicates that $R^2$ may be in either the cis or trans orientation relative to the moiety -A*—COOZ.

In formula (1), A* is a single bond, or a linear $C_{1-6}$ or branched or cyclic $C_{3-8}$ alkylene group, wherein if the carbon number of the alkylene group is two or more, then the alkylene group may contain 1 to 3 heteroatoms, wherein each heteroatom is located in between two carbon atoms of the alkylene carbon chain, which heteroatoms are selected from an oxygen atom, nitrogen atom, and sulfur atom, and/or which alkylene group may contain in between two carbon atoms of the alkylene carbon chain 1 to 3 groups selected from an amide bond or a urethane bond. A* may be a single bond, or a linear $C_{1-6}$ or branched $C_{3-8}$ alkylene group, wherein if the carbon number of the alkylene group is two or more, then the alkylene group may contain a heteroatom in between two carbon atoms of the alkylene carbon chain, which heteroatom is selected from an oxygen atom or a nitrogen atom, and/or which alkylene group may contain in between two carbon atoms of the alkylene carbon chain a group selected from an amide bond or a urethane bond. A* may be a single bond or a linear $C_{1-6}$ alkylene group, A* may be a single bond.

In formula (1), Z which may be the same or different, independently represents a hydrogen atom, a metal ion, a protecting group for a carboxylic acid group, or the Z forms with a further —COOZ group present in the molecule an intramolecular anhydride group. The metal ion may be a monovalent metal ion such as an alkali metal ion. In one embodiment, Z is a protecting group for a carboxylic acid group. In another embodiment, Z is a hydrogen atom. When Z forms with a further —COOZ group present in the molecule an intramolecular anhydride group (—C(O)OC(O)—), the further —COOZ group may be present on $R^1$ such as in case of itaconic acid anhydride.

In one embodiment, Z is a hydrogen atom and the polymerization reaction is conducted in an alkaline environment. In an alternative embodiment, Z is a hydrogen atom and the carboxylic acid groups of the first polymerizable monomer and/or the hydroxyl groups of the second copolymerizable monomer carry a protecting group.

According to one embodiment of the present disclosure, the first polymerizable monomer is a compound represented by the general formula (1'):

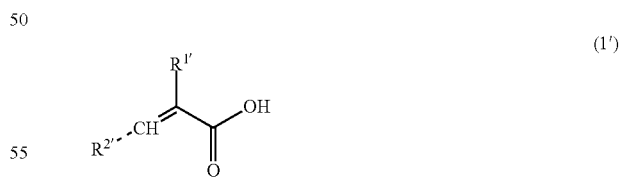

(1')

wherein $R^{1'}$ is a hydrogen atom, or a linear $C_{1-4}$ or branched or cyclic $C_{3-6}$ alkyl group which may be substituted with a —COOH group, $R^{2'}$ is a hydrogen atom, or a linear $C_{1-4}$ or branched or cyclic $C_{3-6}$ group which may be is substituted with a —COOH group, $R^{1'}$ and $R^{2'}$ may be selected with the proviso that the molecular weight of the first polymerizable monomer is at most 200 Da, such as at most 150 Da.

The compound of formula (1') may be selected from the group consisting of itaconic acid, (meth)acrylic acid, maleic acid or an anhydride thereof. The compound of formula (1') may be (meth)acrylic acid or the intramolecular anhydride of itaconic acid or maleic acid, or the compound of formula (1') may be acrylic acid or the intramolecular anhydride of itaconic acid.

According to another embodiment of the present disclosure, the first polymerizable monomer is a compound represented by the general formula (1"):

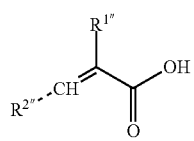

(1")

wherein
R$^{1''}$ is a hydrogen atom, or a linear C$_{1-3}$ or branched C$_{3-5}$ alkyl group, and
R$^{2''}$ is a hydrogen atom, or a linear C$_{1-3}$ or branched C$_{3-5}$ alkyl group which may be substituted with a —COOH group, wherein R$^{1''}$ and R$^{2''}$ are selected with the proviso that the molecular weight of the compound of formula (1") is at most 200 Da;
such as,
R$^{1''}$ is a hydrogen atom, and
R$^{2''}$ is a hydrogen atom, or a linear C$_{1-3}$ or branched C$_{3-5}$ alkyl group optionally substituted with a —COOH group, wherein R$^{1''}$ and R$^{2''}$ are selected with the proviso that the molecular weight of the compound of formula (1") is at most 150 Da;
or such as,
R$^{1''}$ is a hydrogen atom, and
R$^{2''}$ is a hydrogen atom, or a methyl group substituted with a —COOH group,
wherein R$^{1''}$ and R$^{2''}$ are selected with the proviso that the molecular weight of the compound of formula (1") is at most 150 Da.

The compound of formula (1") may be itaconic acid, acrylic acid or an anhydride thereof, or it may be acrylic acid and the intramolecular anhydride of itaconic acid.

The optional second copolymerizable monomer is represented by the general formula (2):

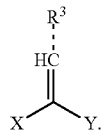

(2)

In formula (2), R$^3$ is a hydrogen atom, or a linear C$_{1-6}$ or branched or cyclic C$_{3-8}$ alkyl group which may be substituted with a —COOZ' group. R$^3$ may be a hydrogen atom. In formula (2), the dotted line indicates that R$^3$ may be in either the cis or trans orientation relative to group X.

In formula (2), X is a protected hydroxyl or amino group or a hydrocarbon group having 1 to 20 carbon atoms, which is substituted with a hydroxyl and/or amino group which may carry a protecting group, wherein the hydrocarbon group may contain 1 to 6 heteroatoms, which heteroatoms are selected from an oxygen atom, nitrogen atom, and sulfur atom, and/or which hydrocarbon group may contain a group selected from an amide bond or a urethane bond and which hydrocarbon group may further be substituted with up to 6 groups selected from —COOZ', amino groups, hydroxyl groups and thiol groups. X may be a hydrocarbon group having 1 to 20 carbon atoms, which is substituted with a hydroxyl group which may carry a protecting group, wherein the hydrocarbon group may contain a heteroatom, which heteroatom is selected from an oxygen atom and a nitrogen atom, and/or which hydrocarbon group may contain a group selected from an amide bond or a urethane bond and which hydrocarbon group may further be substituted with a —COOZ' group. Or, X may be a hydrocarbon group having 1 to 20 carbon atoms, such as 1 to 6 carbon atoms, which is substituted with a hydroxyl group which may carry a protecting group, wherein the hydrocarbon group may contain an oxygen atom and/or which hydrocarbon group may contain an amide bond and which hydrocarbon group may further be substituted with a —COOZ' group. In a specific embodiment wherein X is a protected hydroxyl group, the compound of formula (2) is allyl alcohol, wherein the hydroxyl group may carry a protecting group in the form of an allyl group.

In X of In X of formula (2), the hydrocarbon group having 1 to 20 carbon atoms may be a linear C$_{1-20}$ or branched or cyclic C$_{3-20}$ alkyl group, or a C$_{6-20}$ aryl group. The protecting group of a(n) (optionally) protected hydroxyl or amino group is not particularly limited and may be any conventional protecting group for an amino group as, for example, described in P. G. M. Wuts and T. W. Greene, Greene's Protective Groups in Organic Synthesis, 4$^{th}$ Edition, John Wiley and Sons Inc., 2007.

The hydroxyl-protecting group may be selected from the group consisting of alkyl, alkenyl, benzyl, benzoyl, methoxymethyl (MOM), tetrahydropyranyl (THP), tert-butyldimethylsilyl (TBDMS), tert-butyldiphenylsilyl (TBDPS), acetyl, pivalalyl. The hydroxyl-protecting group may be selected from the group consisting of C1-6 alkyl, C2-6 alkenyl, benzyl, benzoyl, acetyl and pivalyl, or the hydroxyl-protecting group may be selected from the group consisting of tert-butyl, vinyl, allyl, benzyl, benzoyl, acetyl and pivalyl.

Suitable structures are exemplified in Scheme 1 below wherein a hydroxyl group may also carry a protecting group.

Scheme 1

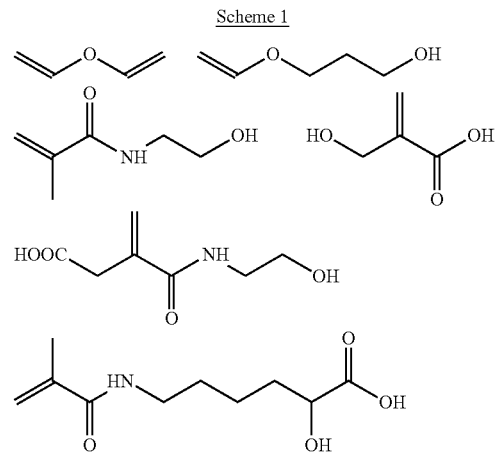

The optional amino-protecting group may be selected from an acyl group, an arylalkyl group, an alkoxy carbonyl group, and an aryloxycarbonyl group. In embodiments, the amino-protecting group may be an acyl group, or the amino-protecting group may be a formyl group.

In embodiments, the second copolymerizable monomer comprising one or more optionally protected amino groups is selected from allyl amine, aminopropyl vinyl ether, aminoethyl vinyl ether, N-vinyl formamide and 2-aminomethyl acrylic acid. In one embodiment, the second copolymerizable monomer is aminopropyl vinyl ether. The amino group may be in the form of an ammonium salt such as an ammonium chloride. Suitable structures where the amino group may also carry a protecting group are depicted in Scheme 2 below.

Scheme 2

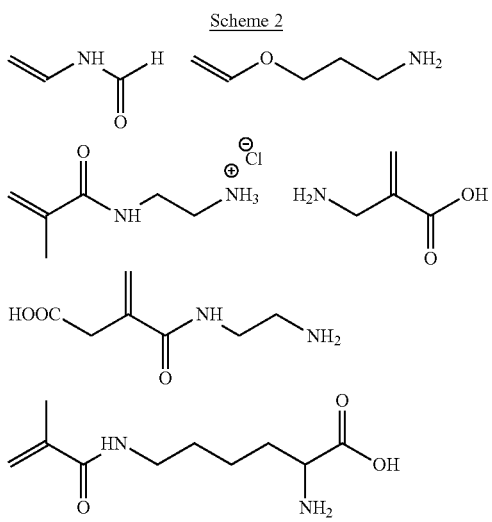

In formula (2), Y may be a hydrogen atom, a —COOZ' group, or a hydrocarbon group having 1 to 20 carbon atoms, for example the hydrocarbon group may contain 1 to 6 heteroatoms, which heteroatoms are selected from an oxygen atom, nitrogen atom, and sulfur atom, and/or which hydrocarbon group may contain a group selected from an amide bond or a urethane bond and which hydrocarbon group may further be substituted with up to 6 groups selected from —COOZ', amino groups, hydroxyl groups and thiol groups. In embodiments, Y is a hydrogen atom, a —COOZ' group, or a hydrocarbon group having 1 to 20 carbon atoms, wherein the hydrocarbon group may contain a heteroatom, which heteroatom is selected from an oxygen atom and a nitrogen atom, and/or which hydrocarbon group may contain a group selected from an amide bond or a urethane bond and which hydrocarbon group may further be substituted with a —COOZ' group. In embodiments, Y is a hydrogen atom or a hydrocarbon group having 1 to 20 carbon atoms, such as 1 to 6 carbon atoms, wherein the hydrocarbon group may contain an oxygen atom and/or which hydrocarbon group may contain an amide bond and which hydrocarbon group may further be substituted with a —COOZ' group. In one embodiment, Y is a hydrogen atom.

In Y of formula (2), the hydrocarbon group having 1 to 20 carbon atoms may be a linear $C_{1-20}$ or branched or cyclic $C_{3-20}$ alkyl group, or a $C_{6-20}$ aryl group.

In formula (2), Z' which may be the same or different, independently represents a hydrogen atom, a metal ion, a protecting group for a carboxylic acid group, or the Z' forms with a further —COOZ' group present in the molecule an intramolecular anhydride group. In one embodiment, Z' is a protecting group for a carboxylic acid group. In another embodiment, Z' is a hydrogen atom. The metal ion may be a monovalent metal ion such as an alkali metal ion. In another embodiment, Z' is a hydrogen atom. When Z forms with a further —COOZ' group present in the molecule an intramolecular anhydride group (—C(O)OC(O)—).

In an embodiment, Z' is a hydrogen atom and the polymerization reaction is conducted in an alkaline environment. In an alternative embodiment, Z' is a hydrogen atom and the hydroxyl groups of the second copolymerizable monomer carry a protecting group.

The second copolymerizable monomer may be represented by the general formula (2'):

wherein $R^{3'}$ is a hydrogen atom;

X' is a protected hydroxyl or amino group or a hydrocarbon group having 1 to 6 carbon atoms, which is substituted with a hydroxyl and/or amino group which may carry a protecting group which hydrocarbon group may further be substituted with a —COOH group;

Y' is a hydrogen atom, a —COOH group or a hydrocarbon group having 1 to 6 carbon atoms, which hydrocarbon group may further be substituted with a —COOH group.

In alternative embodiments, the second copolymerizable monomer may be represented by the general formula (2"):

wherein $R^{3''}$ is a hydrogen atom;

X" is a protected hydroxyl or amino group or a hydrocarbon group having 1 to 3 carbon atoms, which is substituted with a hydroxyl and/or amino group which may carry a protecting group, which hydrocarbon group may contain an amide bond and which hydrocarbon group may further be substituted with a —COOH group;

Y" is a hydrogen atom, a —COOH group or a hydrocarbon group having 1 to 3 carbon atoms, which hydrocarbon group may further be substituted with a —COOH group.

If X, X' and X" of formulae (2), (2') and (2") is a hydrocarbon group substituted with a hydroxyl group and an amino group, then either the hydroxyl group or the amino group may be protected, or both hydroxyl and amino group may be protected with protecting groups which can be selectively removed under different conditions.

In embodiments, in formulae (2), (2') and (2"), X, X' and X" respectively is a protected hydroxyl or amino group or a hydrocarbon group as defined in formulae (2), (2') and (2") above, which hydrocarbon group is substituted with a hydroxyl group or an amino group which may carry a protecting group.

In further embodiments, in formulae (2), (2') and (2"), X, X' and X" respectively is a protected hydroxyl group or a hydrocarbon group as defined in formulae (2), (2') and (2") above, which hydrocarbon group is substituted with a hydroxyl group which may carry a protecting group.

The molar ratio of first polymerizable monomer to second copolymerizable monomer in the mixture copolymerized in step a) (mol first polymerizable monomer/mol second copolymerizable monomer) is in the range of from 100:1 to 100:50, such as in the range from 100:2 to 100:20 or in a range from 100:3 to 100:10.

The further copolymerizable monomers optionally to be used in step a) comprise at least one, such as one to three or one or two, or one optionally protected acidic group(s) which are not carboxylic acid groups. Specific examples of acidic groups are sulfonic acid groups (—$SO_3M$), phosphonic acid groups (—$PO_3M_2$) or phosphoric acid ester groups (—$OPO_3M_2$), or salts thereof, wherein M may independently be a hydrogen atom or a monovalent ion such as an alkali metal or an ammonium ion.

Specific examples of the optional further monomers are selected from 2-acrylamido-2-methylpropane sulfonic acid, vinyl phosphonate, and vinyl sulfonic acid.

Step a) of the aqueous dental glass ionomer composition proceeds as a chain-growth polymerization. In case in step (i) of step a), two different first polymerizable monomers are polymerized, or optional step (ii) is applied, radical copolymerization proceeds, whereby a water-soluble copolymer is obtained.

The type of copolymer formed by step a) of the present disclosure may be a statistical copolymer, a random copolymer, an alternating copolymer, a block copolymer or a combination thereof.

For example, a copolymer obtained by step a) comprising step (ii) is an optionally protected hydroxyl group containing copolymer, such as, for example, a copolymer obtainable by copolymerization of an acrylate and divinyl ether.

The reaction conditions of the polymerization reaction according to step a) of the present disclosure are not particularly limited. Accordingly, it is possible to carry out the reaction in the presence or absence of a solvent. A suitable solvent may be selected from the group of water, dimethyl formamide (DMF), tetrahydrofurane (THF), and dioxane.

The reaction temperature is not particularly limited. The reaction may be carried out at a temperature of between −10° C. to the boiling point of the solvent, such the range of from 0° C. to 80° C.

The reaction time is not particularly limited. In embodiments, the reaction time is in the range of from 10 minutes to 48 hours, such as from 1 hour to 36 hours.

The reaction may be carried out in the presence of a polymerization initiator. In one embodiment of the aqueous dental glass ionomer composition, the polymerization initiator is selected from azobisisobutyronitrile (AIBN), 2,2-azobis(2-amidinopropane)dihydrochloride, 2,2'-azobis(2-methylbutyronitrile), 2,2'-azobis(N,N'-dimethyleneisobutyramidine) dihydrochloride, and 4,4'-azobis(4-cyano pentanoic acid). The amount of the polymerization initiator is not particularly limited. Suitably, the amount may be in the range of from 0.001 to 5 mol % based on the total amount of the monomers.

In embodiments, in step a), the obtained water-soluble polymer does not comprise a pendant ß-dicarbonyl group The reaction product obtained in step a) may be isolated by precipitation and filtration, or lyophilization. The product may be purified according to conventional methods.

Step b) of the aqueous dental glass ionomer composition is a step of coupling a compound having a polymerizable moiety and a functional group reactive with a carboxylic acid group of repeating units derived from the first polymerizable monomer or a functional group reactive with an optionally protected hydroxyl and/or amino group of repeating units derived from the second copolymerizable monomer to the water-soluble polymer obtained in step a), wherein the optionally protected carboxylic acid or hydroxyl group is deprotected.

According to the present disclosure, in step b), one or a mixture of two or more compounds having a polymerizable moiety and a functional group reactive with a carboxylic acid group of repeating units derived from the first polymerizable monomer or a functional group reactive with an optionally protected hydroxyl and/or amino group of repeating units derived from the second copolymerizable monomer to the water-soluble polymer obtained in step a) may be used.

The coupling reaction in step b) is a condensation reaction or an addition reaction forming a linking group selected from an ester or urethane group.

The term "functional group reactive with optionally protected carboxylic acid group of repeating units derived from the first polymerizable monomer or an optionally protected hydroxyl and/or amino group of repeating units derived from the second copolymerizable monomer in the water-soluble polymer obtained in step a)" as used herein means any group which can form a covalent bond with a carboxyl or hydroxyl group of the water-soluble, polymerizable polymer comprising acidic groups according to (B).

If one or more of the carboxyl and optional hydroxyl groups of repeating units derived from the first polymerizable monomer and second copolymerizable monomer in the water-soluble (co)polymer obtained in step a) is protected, the at least one or more carboxyl and optional hydroxyl group can be deprotected prior to step b) or concomitant with step b).

The conditions for deprotection of an optionally protected carboxyl or hydroxyl group are selected according to the protecting group used. In embodiments, the protected carboxyl or hydroxyl group is deprotected by hydrogenolysis or treatment with acid or base.

If the deprotection of a protected carboxyl or hydroxyl group is carried out concomitantly with step b), it will be understood by a person skilled in the art that the deprotection conditions and the conditions for step b) have to be selected so that both reactions can proceed efficiently.

In one embodiment of the aqueous dental glass ionomer composition, the compound having a polymerizable moiety and a functional group reactive with an optionally protected carboxylic acid group or a hydroxyl and/or amino group of repeating units derived from the second copolymerizable monomer is a compound represented by the general formula (3) or (4):

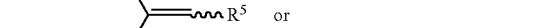

In formulae (3) and (4), the jagged line indicates that $R^5$ or $R^6$ may be in either the cis or trans orientation relative to the carbonyl group of formula (3) or group -$A^\#$ $G^\#$ of formula (4).

With compound of formula (3), polymerizable pendant groups are linked to the backbone of the water-soluble polymer by forming ester or amide bonds with the carboxylic acid groups of the water-soluble polymer obtained in step (a).

In formula (3), G is a hydroxyl group or an amino group, which group may carry a protecting group. The protecting group of the (optionally) protected hydroxyl group may be any conventional protecting group for a hydroxyl group, such as those described above in relation with compound of formula (2). The protecting group of the (optionally) protected amino group may be any is not particularly limited as long as it is an amino-protecting group known to those of ordinary skill in the art of organic chemistry, e.g. from P. G. M. Wuts and T. W. Greene, Greene's Protective Groups in Organic Synthesis, 4th Edition, John Wiley and Sons Inc., 2007. The amino-protecting group may be selected from the group consisting of an acyl group, an arylalkyl group, an alkoxy carbonyl group, and an aryloxycarbonyl group. In embodiments, the amino-protecting group may be an acyl group, or the amino-protecting group may be a formyl group.

In formula (3), if G is an optionally protected hydroxyl group, then E is an oxygen atom and G is OR, and if G is an optionally protected amino group, then E is a secondary amino group (NH) or a tertiary amino group $NR^\#$ wherein $R^\#$ is a linear $C_{1-6}$ or branched or cyclic $C_{3-8}$ alkyl group.

Further, in formula (3), $R^4$ is a hydrogen atom or a linear $C_{1-6}$ or branched or cyclic $C_{3-8}$ alkyl group which may be substituted with a —COOZ" group, and $R^5$ is a hydrogen atom, or a linear $C_{1-6}$ or branched or cyclic $C_{3-8}$ alkyl group which may be substituted with a —COOZ" group. In embodiments, $R^4$ may be a hydrogen atom, and $R^5$ is a hydrogen atom or a methyl group. In further embodiments, $R^4$ is a hydrogen atom, and $R^5$ is a methyl group.

In formula (3), Z" which may be same or different, independently represents a hydrogen atom, a metal ion, a protecting group for a carboxylic acid group, or the Z" forms with a further —COOZ" group present in the molecule an intramolecular anhydride group.

In one embodiment, Z" is a protecting group for a carboxylic acid group. In another embodiment, Z" is a hydrogen atom. In an embodiment, Z" is a hydrogen atom and the polymerization reaction is conducted in an alkaline environment. In an alternative embodiment, Z" is a hydrogen atom and the hydroxyl groups of the second copolymerizable monomer carry a protecting group.

In formula (3), L is a linking group representing a linear $C_{1-15}$ or branched or cyclic $C_{3-15}$ alkylene group, wherein if the carbon number of the alkylene group is two or more, then the alkylene group may contain 1 to 3 heteroatoms, wherein each heteroatom is located in between two carbon atoms of the alkylene carbon chain, which heteroatoms are selected from an oxygen atom, nitrogen atom, and sulfur atom, and/or which alkylene group may contain, if its carbon number is two or more, in between two carbon atoms of the alkylene carbon chain 1 to 3 groups selected from an amide bond or a urethane bond. In embodiments, L is a —[$C_{1-5}$ alkylene-Het]$_n$—($C_{1-5}$ alkylene)- group wherein Het is a nitrogen or an oxygen atom and with n=0 to 3, such as L is a linear $C_{1-5}$ or branched $C_{3-5}$ alkylene. In other embodiments, L is methylene or ethylene.

Further, in formula (3), E is an oxygen atom or a secondary amino group (NH) or a tertiary amino group $NR^\#$ wherein $R^\#$ is a linear $C_{1-6}$ or branched or cyclic $C_{3-8}$ alkyl group.

It may be desired that the compound of formula (3) wherein G is an optionally protected hydroxyl group and E is an oxygen atom is selected from the group consisting of 3-hydroxypropyl acrylate, 3-hydroxypropyl methacrylate, 2-hydroxyethyl acrylate, 2-hydroxyethyl methacrylate (HEMA), or a C1-6 alkyl ether thereof. In embodiments, the compound of formula (3) is 2-hydroxyethyl acrylate or 2-hydroxyethyl methacrylate (HEMA).

With compound of formula (4), polymerizable pendant groups are linked to the backbone of the water-soluble polymer by forming ester or urethane bonds with the hydroxyl group of the water-soluble polymer obtained in step (a), and/or by forming amide bonds with the amino group of the water-soluble polymer obtained in step (a).

In formula (4), $G^\#$ is —N=C=O or —CO-LG wherein LG is a leaving group or wherein LG may replace Z''' and form with $R^6$ or $R^7$ an intramolecular carboxylic acid anhydride group, or wherein two molecules of formula (4) form an intermolecular carboxylic acid anhydride group by condensation of LG and/or —COOZ''', wherein LG is an oxygen atom.

If $G^\#$ is —CO-LG, LG is a hydroxyl group, a chlorine atom or a bromine atom, or forms with the adjacent carbonyl group a carboxylic acid anhydride moiety. In embodiments, LG is a group which is suitable for reacting the compound of formula (4) in a Schotten-Baumann type reaction.

In another embodiment, LG may replace Z''' and form with $R^6$ or $R^7$ an intramolecular carboxylic acid anhydride group.

In yet another embodiment, two molecules of formula (4) form an intermolecular carboxylic acid anhydride group by sharing a common LG, wherein LG is an oxygen atom.

Further, in formula (4), $A^\#$ is a single bond, or a linear $C_{1-15}$ or branched or cyclic $C_{3-15}$ alkylene group which is bonded to the carbon-carbon bond of formula (4) via a single bond or a carbonyl group (—CO—), wherein if the carbon number of the alkylene group is two or more, then the alkylene group may contain 1 to 3 heteroatoms, wherein each heteroatom is located in between two carbon atoms of the alkylene carbon chain, which heteroatoms are selected from an oxygen atom, nitrogen atom, and sulfur atom, and/or which alkylene group may contain, if its carbon number is two or more, in between two carbon atoms of the alkylene carbon chain 1 to 3 groups selected from an amide bond or a urethane bond. In embodiments, $A^\#$ is a single bond, a linear $C_{1-6}$ or branched $C_{3-8}$ alkylene group or a —CO— [Het-$C_{1-5}$ alkylene]$_n$- group wherein Het is a secondary amino group (NH) or an oxygen atom with n=1 to 3, and the $C_{1-5}$ alkylene group includes linear $C_{1-5}$ and branched $C_{3-5}$ alkylene groups. In further embodiments, A # is a single bond, a methylene or ethylene group or a —CO-Het-$C_{1-3}$ alkylene group.

In formula (4), $R^6$ is a hydrogen atom, a —COOZ''' group, or a linear $C_{1-6}$ or branched or cyclic $C_{3-8}$ alkyl group which may be substituted with a —COOZ''' group, and $R^7$ is a hydrogen atom, a —COOZ''' group or a linear $C_{1-6}$ or branched $C_{3-6}$ alkyl group which may be substituted with a —COOZ''' group. In embodiments, $R^6$ is a hydrogen atom, and $R^7$ is a hydrogen atom or a methyl group, or $R^6$ is a hydrogen atom, and $R^7$ is a methyl group.

In formula (4), Z''' which may be same or different, independently represents a hydrogen atom, a metal ion, a protecting group for a carboxylic acid group, or the Z''' forms with a further —COOZ''' group present in the molecule an intramolecular anhydride group.

In one embodiment, Z''' is a protecting group for a carboxylic acid group. In another embodiment, Z''' is a hydrogen atom. In an embodiment, Z" is a hydrogen atom and the polymerization reaction is conducted in an alkaline environment. In an alternative embodiment, Z''' is a hydrogen atom and the hydroxyl groups of the second copolymerizable monomer carry a protecting group.

It is desired that the compound of formula (4) may be selected from the group consisting of acrylic acid, methacrylic acid, crotonic acid, isocrotonic acid, tiglic acid, angelic acid, itaconic acid, maleic acid, or a bromide, a chloride or an anhydride of the aforementioned acids formed of two identical or different acids; or an anhydride of the aforementioned acids formed of two identical acids. In embodiments, the compound of formula (4) is (meth)acrylic anhydride or and intermolecular anhydride of itaconic acid or maleic acid.

According to another embodiment, the compound of formula (4) is a carboxylic acid selected from the group consisting of acrylic acid, (meth)acrylic acid, crotonic acid, isocrotonic acid, tiglic acid, angelic acid, itaconic acid, maleic acid or an anhydride of the aforementioned acids formed of two identical or different acids; such an anhydride of the aforementioned acids formed of two identical acids. In further embodiments, the compound of formula (4) is (meth)acrylic anhydride or an intramolecular anhydride of itaconic acid or maleic acid, such as the intramolecular anhydride of itaconic acid.

The compound of formula (4) may be represented by the general formula (4'):

wherein
$G^{\#'}$ is —N=C=O or —COOH,
$R^{6'}$ is a hydrogen atom, or a linear $C_{1-4}$ or branched or cyclic $C_{3-6}$ alkyl group which may be substituted with a —COOH group,
$R^{7'}$ is a hydrogen atom, or a linear $C_{1-4}$ or branched $C_{3-6}$ alkyl group which may be substituted with a —COOH group,
wherein if $G^{\#'}$ is —N=C=O, then $R^{6'}$ and $R^{7'}$ are not substituted with a —COOH group.

In compound of formula (4'), $R^{6'}$ and $R^{7'}$ are selected with the proviso that the molecular weight of compound of formula (4') is at most 200 Da, such as at most 150 Da, It is desired that compound of formula (4') is vinyl isocyanate, (meth)acrylic acid or the anhydride thereof, or the intramolecular anhydride of itaconic acid or maleic acid.

In embodiments, the compound of formula (4') may be represented by a compound of the general formula (4"):

wherein
$G^{\#''}$ is —N=C=O or —COOH
$R^{6''}$ is a hydrogen atom, or a linear $C_{1-3}$ or branched $C_{3-5}$ alkyl group, and
$R^{7''}$ is a hydrogen atom, or a linear $C_{1-3}$ or branched $C_{3-5}$ alkyl group which may be substituted with a —COOH group, wherein $R^{6''}$ and $R^{7''}$ are selected with the proviso that the molecular weight of the compound of formula (4") is at most 200 Da;
or, in embodiments,
$R^{6''}$ is a hydrogen atom, and
$R^{7''}$ is a hydrogen atom, or a linear $C_{1-3}$ alkyl or branched $C_{3-5}$ group optionally substituted with a —COOH group, wherein $R^{6''}$ and $R^{7''}$ are selected with the proviso that the molecular weight of the compound of formula (4") is at most 150 Da;
or in further embodiments,
$R^{6''}$ is a hydrogen atom, and
$R^{7''}$ is a hydrogen atom, or a methyl group optionally substituted with a —COOH group, wherein $R^{6''}$ and $R^{7''}$ are selected with the proviso that the molecular weight of the compound of formula (4) is at most 150 Da,
wherein if $G^{\#''}$ is —N=C=O, then $R^{6''}$ and $R^{7''}$ are not substituted with a —COOH group.

In embodiments, the compound of formula (4") is vinyl isocyanate, or (meth)acrylic acid or the anhydride thereof.

In embodiments, in step b), the water-soluble polymer is reacted with compound of formula (3) wherein G is a hydroxyl group. In embodiments, in step a), in the water-soluble polymer obtained, all carboxylic acid groups are protected, which water-soluble polymer is reacted in step b) with the compound of formula (4).

The coupling according to step b) of the present disclosure serves to introduce one or more polymerizable moieties into the water-soluble polymer obtained in step a), which moieties can be post-polymerized to provide additional covalent and advantageously also ionic crosslinking, imparting additional strength to the dental material.

In one embodiment of the aqueous dental glass ionomer composition, the carboxylic acid groups and the optional hydroxyl groups of the polymer obtained in step b) are not protected and the copolymer can be used as a polymer according to the present disclosure without further treatment. In an alternative embodiment, at least a part of the carboxylic acid and the optional hydroxyl groups of the polymer obtained in step b) are protected and the protected carboxylic acid groups have to be deprotected before the copolymer exhibits the features of a polymer according to the present disclosure.

The reaction conditions of the reaction according to step b) of the present disclosure are not particularly limited. Accordingly, it is possible to carry out the reaction in the presence or absence of a solvent. A suitable solvent may be selected from the group of dimethyl formamide (DMF), tetrahydrofurane (THF), and dioxane.

The reaction temperature is not particularly limited. In embodiments, the reaction is carried out at a temperature of between −10° C. to the boiling point of the solvent, such in the range of from 0° C. to 80° C.

The reaction time is not particularly limited. In embodiments, the reaction time is in the range of from 10 minutes to 48 hours, such as 1 hour to 36 hours.

The reaction product obtained in step b) may be isolated by precipitation and filtration. The product may be purified.

The aqueous dental glass ionomer composition optionally includes a step of deprotecting the protected carboxylic acid group after step a) or step b), for obtaining a polymerizable polymer. In an embodiment, the aqueous dental glass ionomer composition includes a step of deprotecting the protected carboxylic acid group for obtaining a polymerizable polymer. In a further embodiment, the aqueous dental glass ionomer composition includes a step of deprotecting the protected carboxylic acid group after step b).

The conditions for deprotection of an optionally protected carboxylic acid group are selected according to the protecting group used. In embodiments, the protected carboxylic acid group is deprotected by hydrogenolysis or treatment with acid or base.

A first embodiment of the polymerizable polymer according to (B) is illustrated by the following Scheme 3, wherein an acrylic acid having Z in the form of a protecting group for a carboxylic acid group, is reacted with a compound of formula (1) wherein $R_1$, $R_2$ and Z are hydrogen for obtaining a polymer backbone having a protected carboxylic acid group. The copolymer may be a random copolymer. In a further step, the free carboxylic acid groups are coupled to a compound of formula (3) wherein R, $R^4$ and $R^5$ are hydrogen. Finally, the protected carboxylic acid groups of the polymer backbone are liberated, whereby a polymer of the disclosure is obtained having acidic groups reactive in a cement reaction wherein ionic bonds are formed, and having polymerizable groups reactive in a crosslinking reaction wherein covalent bonds are formed.

A second embodiment of the polymerizable polymer according to (B) is illustrated by the following Scheme 4, wherein a compound of formula (1) wherein $R_1$, $R_2$ and Z are hydrogen is reacted with a compound of formula (1) wherein $R^1$ and $R^2$ are hydrogen and Z forms with a further —COOZ group present in the molecule an intramolecular anhydride group for obtaining a polymer backbone having carboxylic acid groups in the form of carboxylic acid anhydride. The copolymer may be a random copolymer. In a further step, the carboxylic acid anhydride groups are coupled to a compound of formula (3) wherein R, $R^4$ and $R^5$ are hydrogen, whereby a polymer of the disclosure is obtained having acidic groups reactive in a cement reaction wherein ionic bonds are formed, and having polymerizable groups reactive in a crosslinking reaction wherein covalent bonds are formed. This embodiment has the advantage that it can be dispensed with a deprotection step for liberating the protected carboxylic acid groups.

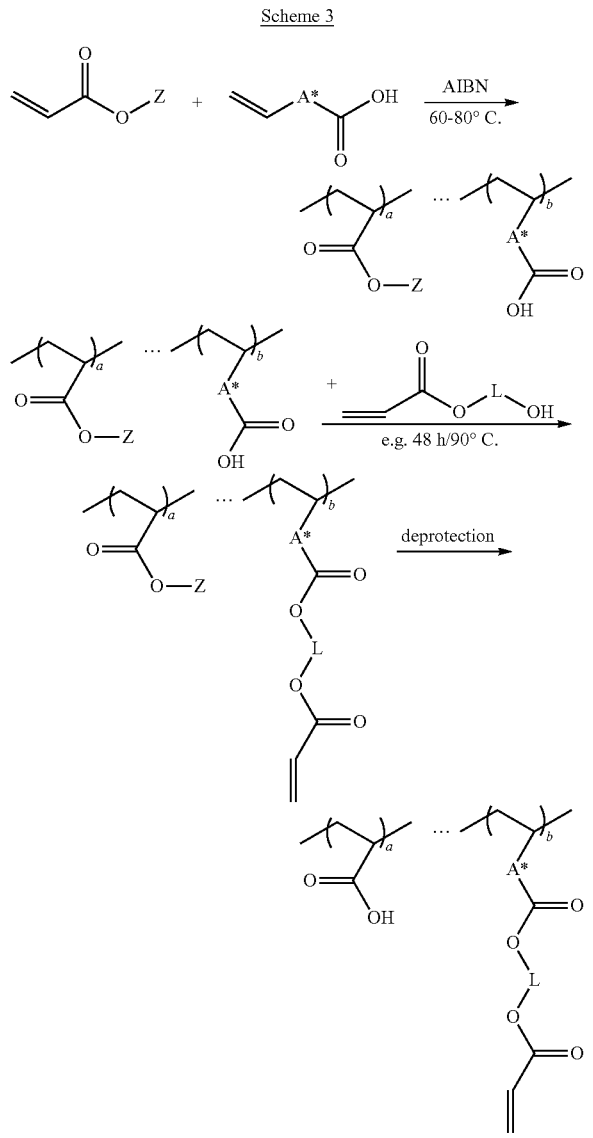

Scheme 3

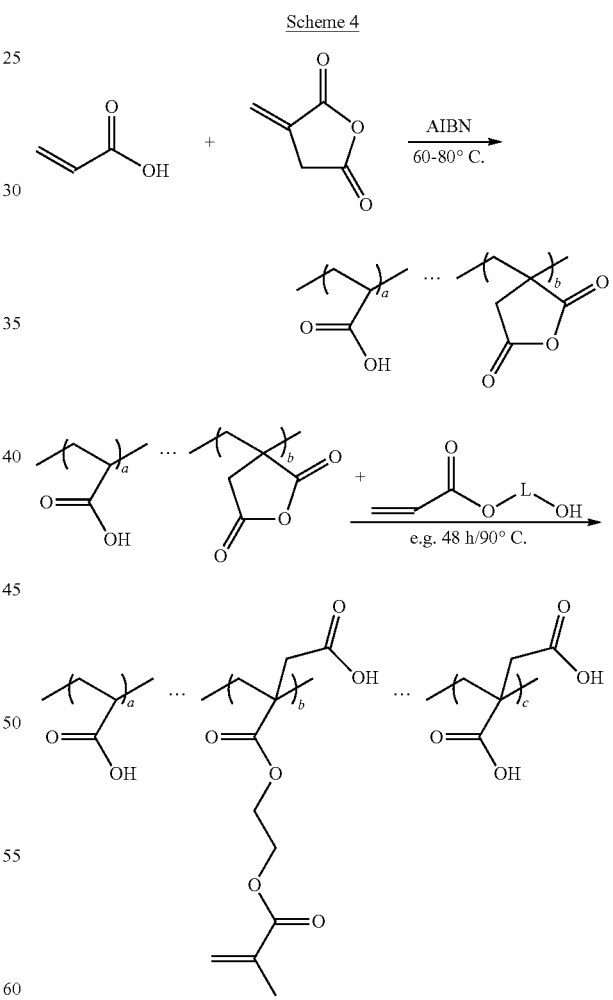

Scheme 4

In above Scheme 3, any acrylester group may be replaced by a methacrylester group.

In above Scheme 4, any methacrylester group may be replaced by a acrylester group.

A third embodiment of the polymerizable polymer according to (B) is illustrated by the following Scheme 5, wherein a compound of formula (1) in the form of protected acrylic acid is reacted with a compound of formula (2) wherein X and Y are hydrogen and R³ is —(CH$_2$)$_2$—OH, for obtaining a hydroxyl group containing polymer backbone. In a further step, the hydroxyl groups of the polymer backbone are coupled to a polymerizable group containing moiety, in this case an acrylic acid derivative capable of coupling to the hydroxyl groups of the polymer backbone, e.g. acrylic acid chloride or bromide or acrylic acid anhydride. Finally, the carboxylic acid groups are liberated whereby a polymer of the disclosure is obtained having acidic groups reactive in a cement reaction wherein ionic bonds are formed, and having polymerizable groups reactive in a crosslinking reaction wherein covalent bonds are formed.

Scheme 5

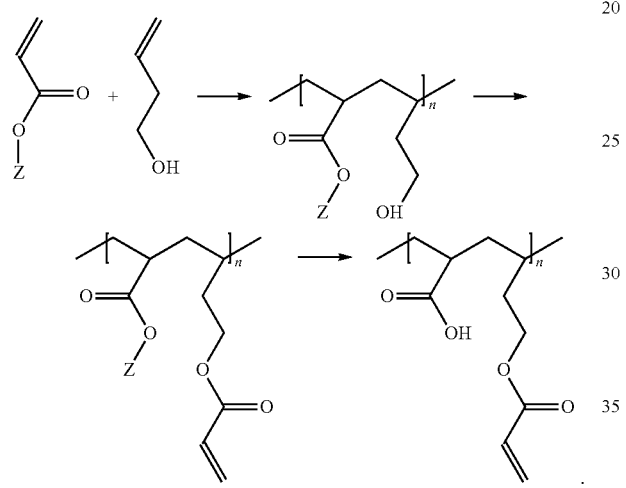

In the above Scheme 5, any acrylamide group may be replaced by a methacrylamide group The polymerizable polymer obtained in step b) may be exemplified by the following structures depicted in Scheme 6 below.

Scheme 6

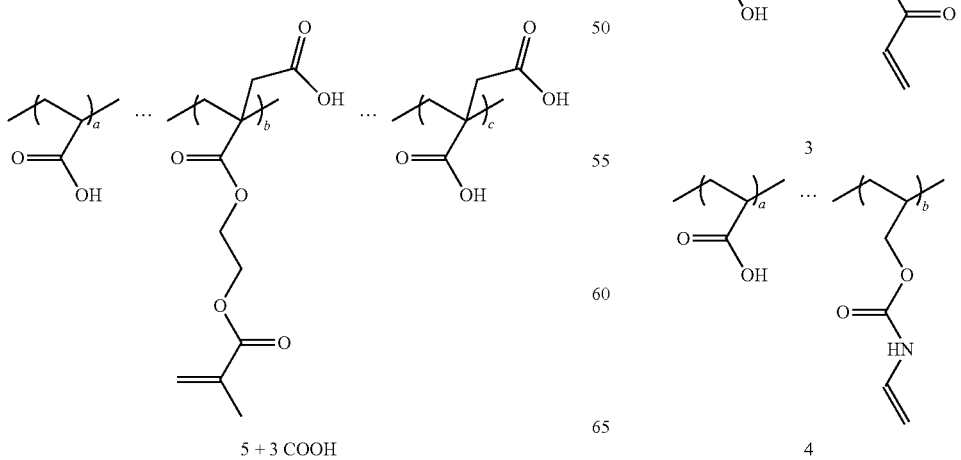

5 + 3 COOH

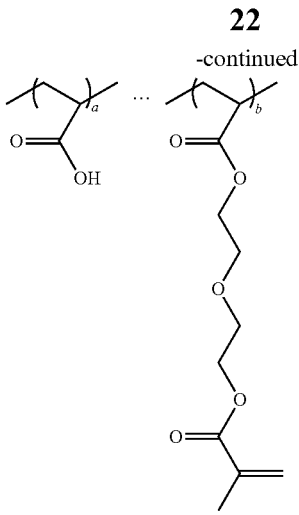

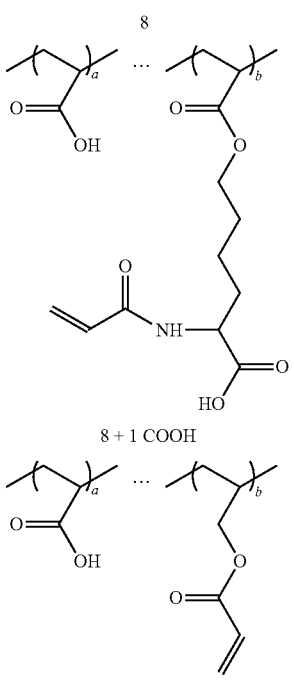

In the structures illustrated in Scheme 6, the numbers refer to the number of additional carbon atoms introduced by each of the side chain as compared to a corresponding polyacrylic acid. Since a polymer having (a+b+c) repeating units contains b+c times the number of additional carbon atoms in addition to the number of carbon atoms in a polyacrylic acid having (a+b+c) carboxylic acid groups, but b+c times less carboxylic acid groups, the water solubility may be reduced. On the other hand, the introduction of an additional ionic group such as a —COOH group is capable of compensating the decrease in water solubility, and is also indicated above. The number of side chains b, the number of additional carbon atoms and the number of additional carboxylic acid groups are adjusted so as to provide a useful water solubility of the polymer of the present disclosure.

Accordingly, in an embodiment, the side chains of the polymer which are linked to the polymer backbone via an ester bond or an urethane bond contain one or more additional acidic groups, such as carboxylic acid groups.

The polymerizable polymer according to (B) may have an average molecular weight $M_w$ in the range of from $10^3$ to $10^6$ Da, such as $10^4$ to $10^6$ Da. In embodiments, the average molecular weight $M_w$ is in the range of from $10^5$ to $7 \cdot 10^5$ Da, or $3 \cdot 10^4$ to $2.5 \cdot 10^5$ Da.

The polymerizable polymer according to (B) must be sufficient in number or percent by weight of carboxylic acid groups to bring about the setting or curing reaction in the presence of the reactive particulate glass according to (A) or any further unmodified or modified particulate reactive(s) and/or non-reactive filler(s). In embodiments, the polymerizable polymer according to (B) is present in the aqueous dental glass ionomer composition in an amount of from 5 to 80 percent by weight, such as 10 to 50 percent by weight, or 15 to 40 percent by weight, based on the total weight of the composition.

(C) The Monomer Having a Single Polymerizable Double Bond

The aqueous dental glass ionomer composition according to the present disclosure comprises a hydrolysis-stable, water-soluble monomer having a single polymerizable double bond and optionally a carboxylic acid group or hydroxyl group. The monomer according to (C) has a single polymerizable double bond, and is hydrolysis-stable and water-soluble.

The term "hydrolysis-stable" used in this connection means that the monomer according to (C) is stable to hydrolysis in an acidic medium, such as in a dental composition. In particular, the monomer according to (C) does not contain groups such as ester groups, and does not hydrolyze in aqueous solution at pH 3 at room temperature within one month.

According to the present disclosure, one or a mixture of two or more hydrolysis-stable, water-soluble monomers according to (C) may be comprised in the aqueous dental glass ionomer composition.

According to an embodiment, the component according to (C) is a hydrolysis-stable, water-soluble monomer, since the monomer according to (C) polymerizes together with the polymerizable polymer according to (B) in the presence of the polymerization initiator system according to (D). Thereby, the monomer according to (C) may polymerize with itself and/or with the polymerizable pendant groups of the polymerizable compound according to (B). Hence, besides of the formation of a polymer formed of the monomer according to (C), there is a graft polymerization wherein monomer(s) according to (C) react with the polymerizable pendant groups of the polymerizable compound according to (B), whereby a graft polymer is formed. Furthermore, the graft side chains formed of the monomer according to (C) may additionally react with the pendant polymerizable groups of another polymerizable polymer according to (B), whereby a crosslinked polymer may be obtained.

In the following Scheme 7, graft polymerisation by means of the monomer according to (C) is exemplary depicted for the polymerizable polymer according to (B) illustrated in Scheme 5 above, wherein N,N-diethyl(meth)acrylamide is merely exemplary selected as monomer according to (C). The letter "m" denotes an integer of at least 1.

Scheme 7

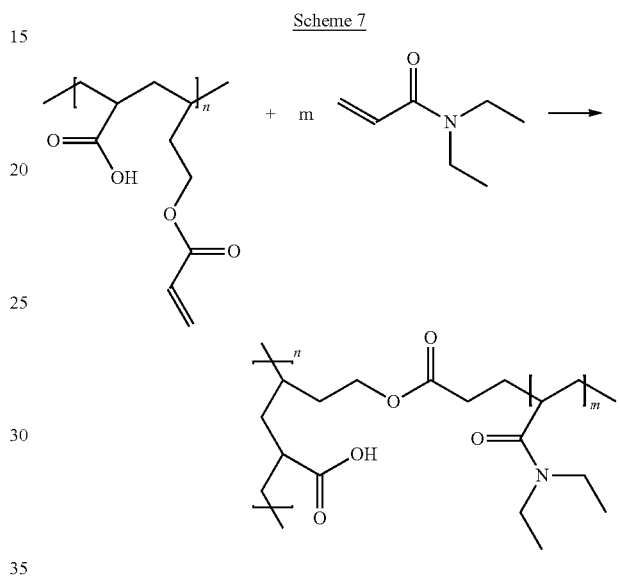

According to the present disclosure, one or a mixture of two or more monomers according to (C) may be used as component (C). A suitable monomer according to (C) does not contain groups hydrolysing at pH 3 within one month. In particular, a suitable monomer according to (C) does not contain any ester group.

Furthermore, a suitable monomer according to (C) has a single polymerizable double bond. Suitable polymerizable double bonds are carbon-carbon double bonds such as alkenyl groups and vinyl groups.

In an embodiment of the aqueous dental glass ionomer composition, the hydrolysis-stable, water-soluble monomer according to (C) is a (meth)acryl monomer, such as a compound represented by the general formula (5):

(5)

In formula (5), the jagged line indicates that $R^\ominus$ may be in either the cis or trans orientation relative to the moiety $-A^\ominus\text{-CO-}G^\ominus$.

In formula (5), $A^\ominus$ is a single bond, or a linear $C_{1-6}$ or branched $C_{3-8}$ alkylene group, wherein if the carbon number of the alkylene group is two or more, then the alkylene group may contain 1 to 3 heteroatoms, wherein each heteroatom is located in between two carbon atoms of the alkylene carbon chain, which heteroatoms are selected from an oxygen atom, nitrogen atom, and sulfur atom, and/or which alkylene group may contain, if its carbon number is two or more, in between two carbon atoms of the alkylene carbon chain 1 to 3 groups selected from an amide bond or a urethane bond. In embodiments, $A^\ominus$ is a single bond, a linear $C_{1-3}$ or branched $C_{3-5}$ alkylene group or a —CO—[Het-$C_{1-5}$ alkylene]$_n$- group wherein Het is a secondary amino group (NH) or an oxygen atom with n=1 to 3, and the $C_{1-5}$ alkylene group includes linear $C_{1-3}$ and branched $C_{3-5}$ alkylene groups. For example, $A^\ominus$ may represent a single bond, a methylene or ethylene group or a —CO-Het-$C_{1-3}$ alkylene group.

Further, in formula (5), $R^\ominus$ or formula (5) is a hydrogen atom, a —COOZ group, or a linear $C_{1-6}$ or branched or cyclic $C_{3-8}$ alkyl group which may be substituted with a —COOZ group. In embodiments, $R^\ominus$ is a hydrogen atom.

$R_{10}$ of formula (5) represents a hydrogen atom, —OM*, —COOM, a linear $C_{1-15}$ or branched $C_{3-18}$ alkyl group which may be substituted with a $C_{3-6}$ cycloalkyl group, a $C_{6-14}$ aryl or $C_{3-14}$ heteroaryl group, —OM*, —COOM, —PO$_3$M, —O—PO$_3$M$_2$ or —SO$_3$M, a $C_{3-18}$ cycloalkyl group which may be substituted with a $C_{1-16}$ alkyl group, a $C_{6-14}$ aryl or $C_{3-14}$ heteroaryl group, —OM*, —COOM, —PO$_3$M, —O—PO$_3$M$_2$ or —SO$_3$M, or a $C_5$ to $C_{18}$ aryl or $C_3$ to $C_{18}$ heteroaryl group which may be substituted with —OM*, —COOM, —PO$_3$M, —O—PO$_3$M$_2$ or —SO$_3$M.

In formula (5), $G^\ominus$ is —OH or a tertiary amino group —NR$_{11}$R*$_{11}$, wherein R$_{11}$ and R*$_{11}$ independently represent a hydrogen atom, a linear $C_{1-18}$ or branched $C_{3-18}$ alkyl group which may be substituted with a $C_{3-6}$ cycloalkyl group, a $C_{6-14}$ aryl or $C_{3-14}$ heteroaryl group, —OM*, —COOM, —PO$_3$M, —O—PO$_3$M$_2$ or —SO$_3$M, a $C_{3-18}$ cycloalkyl group which may be substituted with a $C_{1-16}$ alkyl group, a $C_{6-14}$ aryl or $C_{3-14}$ heteroaryl group, —OM*, —COOM, —PO$_3$M, —O—PO$_3$M$_2$ or —SO$_3$M, or a $C_{5-18}$ aryl or $C_{3-18}$ heteroaryl group which may be substituted with —OM*, —COOM, —PO$_3$M, —O—PO$_3$M$_2$ or —SO$_3$M, wherein R$_{11}$ and R*$_{11}$ may cooperatively form a ring in which R$_{11}$ and R*$_{11}$ may be linked by a C—C bond or a functional group which may be selected from the group consisting of an ether group, a thioether group, an amine group and an amide group. m is an integer, such as in the range from 1 to 10.

In formula (5), M* of R$_{10}$, R$_{11}$ and R*$_{11}$ are independent from each other, each represents a hydrogen atom or a hydroxyl-protecting group, and M of any one R$_{10}$, R$_{11}$ and R*$_{11}$ are independent from each other, each represents a hydrogen atom, a carboxyl-protecting group or a metal atom.

The hydroxyl-protecting group M* may be one as described above for the second polymerizable polymer, and the carboxyl-protecting group M may be one as described above for the first polymerizable monomer.

In embodiments, in case R$_{11}$ and R*$_{11}$ cooperatively form a ring, a 3 to 10 membered ring is formed, such as a 5 to 7 membered ring.

For R$_{10}$, the linear $C_{1-18}$ or branched $C_{3-18}$ alkyl group may e.g. be methyl, ethyl, n-propyl, i-propyl, n-butyl, isobutyl, tert-butyl, sec-butyl, pentyl or hexyl. For R$_{11}$ and R*$_{11}$, the $C_{1-18}$ alkyl group may e.g. be eth(en)yl, n-prop(en)yl, i-prop(en)yl, n-but(en)yl, isobut(en)yl, tert-but(en)yl sec-but (en)yl, pent(en)yl or hex(en)yl.

For R$_{10}$, R$_{11}$ and R*$_{11}$, an aryl group may, for example, be a phenyl group or a naphthyl group, and a $C_{3-14}$ heteroaryl group may contain 1 to 3 heteroatoms selected from nitrogen, oxygen and sulfur.

In embodiments, in formula (5), R$_{10}$ represents a hydrogen atom, —COOM, a linear $C_{1-16}$ or branched $C_{3-16}$ alkyl group which may be substituted with a $C_{3-6}$ cycloalkyl group, a $C_{6-14}$ aryl or $C_{3-14}$ heteroaryl group, —OM*, or COOM, a $C_{3-6}$ cycloalkyl group which may be substituted with a $C_{1-16}$ alkyl group, a $C_{6-14}$ aryl or $C_{3-14}$ heteroaryl group, —OM* or —COOM, a $C_{6-14}$ aryl or $C_{3-14}$ heteroaryl group which may be substituted with —OM*, or —COOM.

In embodiments, in formula (5), R$_{11}$ and R*$_{11}$ independently represent a hydrogen atom, a linear $C_{1-16}$ or branched $C_{3-16}$ alkyl group which may be substituted with a $C_{3-6}$ cycloalkyl group, a $C_{6-14}$ aryl or $C_{3-14}$ heteroaryl group, —OM* or —COOM, a $C_{3-6}$ cycloalkyl group which may be substituted with a $C_{1-16}$ alkyl group, a $C_{6-14}$ aryl or $C_{3-14}$ heteroaryl group, —OM* or —COOM, a $C_{6-14}$ aryl or $C_{3-14}$ heteroaryl group which may be substituted with —OM* or —COOM. In further embodiments, R$_{11}$ and R*$_{11}$ independently represent a hydrogen atom, a linear $C_{1-10}$ or branched $C_{3-10}$ alkyl group which may be substituted with a $C_{4-6}$ cycloalkyl group, a $C_{6-10}$ aryl or $C_{4-10}$ heteroaryl group, a $C_{4-6}$ cycloalkyl group which may be substituted with a $C_{1-6}$ alkyl group, a $C_{6-10}$ aryl or $C_{4-10}$ heteroaryl group, or a $C_{6-10}$ aryl group, wherein R$_{11}$ and R*$_{11}$ may cooperatively form a ring in which R$_{11}$ and R*$_{11}$ may be linked by a C—C bond or a functional group which may be selected from the group consisting of an ether group, a thioether group, an amine group and an amide group. In yet further embodiments, R$_{11}$ and R*$_{11}$ independently represent a hydrogen atom, a linear $C_{1-10}$ or branched $C_{3-10}$ alkyl group which may be substituted with a $C_{6-10}$ aryl group or —OH, a cyclic $C_{3-10}$ alkyl group which may be substituted with —OH, or R$_{11}$" and R*$_{11}$" independently represent a linear $C_{1-10}$ or branched $C_{3-10}$ alkyl group which cooperatively form a ring in which R$_{11}$" and R*$_{11}$" are linked by a C—C bond or an ether group. Yet in further embodiments, R$_{11}$ and R*$_{11}$ represent a linear $C_{1-6}$ or branched $C_{3-6}$ alkyl group which might be substituted with a $C_{6-10}$ aryl group or —OH, a cyclic $C_{3-6}$ alkyl group, or R$_{11}$" and R*$_{11}$" independently represent a linear $C_{1-6}$ or branched $C_{3-6}$ alkyl group which cooperatively form a ring in which R$_{11}$" and R*$_{11}$" are linked by a C—C bond or an ether group. Still even in further embodiments, R$_{11}$ and R*$_{11}$ independently represent a methyl group, an ethyl group, a 2-hydroxyethyl group, a n-propyl group, a benzyl group, an α-methylbenzyl group, a cyclohexyl group, an adamantyl group, or R$_{11}$" and R*$_{11}$" cooperatively form a N-piperidinyl or N-morpholinyl ring. In embodiments, R$_{11}$" and R*$_{11}$" independently represent a methyl or ethyl group.

Monomers according to (C) comprising a carboxylic acid group are particularly advantageous, since such monomers introduce additional carboxylic acid groups into the acidic polymer in the aqueous dental glass ionomer composition, which can undergo a cement reaction resulting in a further improved setting or curing reaction in the presence of the reactive particulate glass according to (A).

In embodiments, in formula (5), $G^\ominus$ is —NR$_{11}$R*$_{11}$. For example, $G^\ominus$ is —NR$_{11}$R*$_{11}$ and $A^\ominus$ is a single bond, that is compound of formula (5) represents a (meth)acrylamide monomer. In embodiments, in formula (5), $G^\ominus$ is —NR$_{11}$R*$_{11}$, $A^\ominus$ is a single bond and $R^\ominus$ is a hydrogen atom, that is compound of formula (5) represents an acrylamide monomer.

In embodiments, the hydrolysis-stable, water-soluble monomer is a (meth)acrylamide monomer of formula (5) selected from the group consisting of:

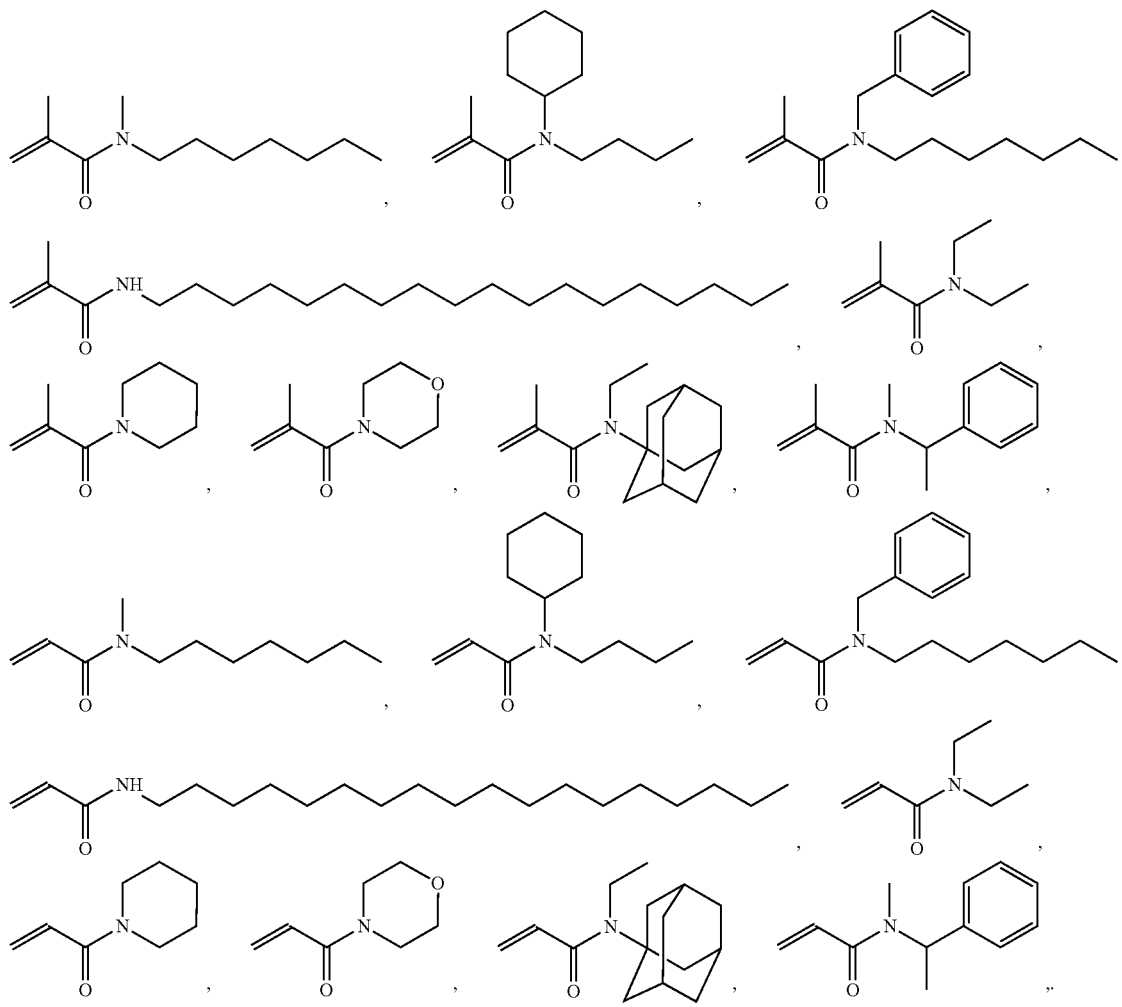

2-hydroxyethyl acrylamide (HEAA), N,N-dimethyl(meth)acrylamide, N,N-di-n-propyl(meth)acrylamide, and N-ethyl-N-methyl(meth)acrylamide.

In embodiments, the hydrolysis-stable, water-soluble monomer compound of formula (5″) is selected from the group consisting of 2-hydroxyethyl acrylamide (HEAA), N,N-dimethyl(meth)acrylamide, N,N-diethyl(meth)acrylamide, N,N-di-n-propyl(meth)acrylamide, and N-ethyl-N-methyl(meth)acrylamide.

In embodiments, in the monomer according to (C) of formula (5), residues $R_{10}$ $R_{11}$ and $R^*_{11}$ are selected with the proviso that the molecular weight of the monomer having a single polymerizable double bond according to (C) is at most 600 Da, such as at most 400 Da, or at most 200 Da, or at most 150 Da, or at most 120 Da.

The monomer according to (C) may be selected in view of a good processability and applicability of the final aqueous dental glass ionomer composition, in particular in terms of viscosity. Therefore, the viscosity of the monomer according to (C) is preferably in the range of from 0.1 to 100 mPa·s, such as from 0.3 to 50 mPa·s, such as from 0.5 to 25 mPa·s, such as from 0.8 to 10 mPa·s, such as from 0.9 to 3 mPa·s.

In embodiments, the monomer according to (C) is contained in the aqueous dental glass ionomer composition in an amount of from 0.1 to 25, such as from 1 to 20 or from 5 to 10 percent by weight based on the total weight of the aqueous dental glass ionomer composition. When the monomer according to (C) is absent, a long-term mechanical resistance may be low. On the other hand, when the amount monomer according to (C) exceeds 25 percent of weight, shrinkage of the dental glass ionomer cement obtained from the present aqueous dental glass ionomer composition may occur. Specifically, by limiting the amount of monomer according to (C) to 10 percent of weight of the aqueous dental glass ionomer composition or less, shrinkage of the dental glass ionomer cement obtained from the present aqueous dental glass ionomer composition can particularly effectively be avoided.

(D) The Polymerization Initiator System

The aqueous dental glass ionomer composition according to the present disclosure comprises a polymerization initiator system. As a polymerization initiator system according to (D), any compound or system, capable of initiating the copolymerization reaction according to the present disclosure may be suitably used. The polymerization initiator according to (D) may be a photoinitiator or a redox initiator or a mixture thereof.

A suitable redox initiator comprises an reducing and oxidizing agents, which produce free-radicals capable of initiating polymerization of polymerizable double bonds in components (B) and (C), independent from the presence of light. The reducing and oxidizing agents are selected so that the polymerization initiator system is sufficiently storage-stable and free of undesirable colorization to permit storage and use under typical dental conditions. Moreover, the reducing and oxidizing agents are selected so that the polymerization initiator system is sufficiently miscible with the resin system to permit dissolution of the polymerization initiator system in the composition.

Useful reducing agents include ascorbic acid, ascorbic acid derivatives, and metal complexed ascorbic acid compounds as described in U.S. Pat. No. 5,501,727; amines, namely tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetra methyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine, salts of a dithionite or sulfite anion, and mixtures thereof.

Suitable oxidizing agents include persulfuric acid and salts thereof, such as ammonium, sodium, potassium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof. One or more different oxidizing agents or one or more different reducing agent may be used in the polymerization initiator system. Small quantities of transition metal compounds may also be added to accelerate the rate of redox cure. The reducing and oxidizing agents are present in amounts sufficient to permit an adequate free-radical reaction rate.

The reducing or oxidizing agents may be microencapsulated for enhancing shelf stability of the composition, and if necessary permitting packaging the reducing and oxidizing agents together (U.S. Pat. No. 5,154,762). Appropriate selection of an encapsulant may allow combination of the oxidizing and reducing agents and even of an acid-functional component and optional filler in a storage-stable state. Moreover, appropriate selection of a water-insoluble encapsulant allows combination of the reducing and oxidizing agents with the particulate reactive glass and water in a storage-stable state.

Suitable photoinitiators for polymerizing free radically photopolymerizable compositions may include binary and tertiary systems. Binary systems may include a photosensitizer and an electron donor compound, and tertiary photoinitiators may include an iodonium salt, a photosensitizer, and an electron donor compound as described in U.S. Pat. No. 5,545,676. Suitable iodonium salts include the diaryl iodonium salts, e.g., diphenyliodonium chloride, diphenyliodonium hexafluorophosphate, diphenyl-iodonium tetrafluoroborate, and tolylcumyliodonium tetrakis(pentafluorophenyl)borate. Suitable photosensitizers are monoketones and diketones that absorb some light within a range of from about 400 nm to about 520 nm (such as from about 450 nm to about 500 nm). Particularly suitable compounds include alpha diketones that have some light absorption within a range of from about 400 nm to about 520 nm (such as from about 450 to about 500 n m). Examples include camphorquinone, benzil, furil, 3,3,6,6-tetramethyl-cyclo-hexanedione, phenanthraquinone, 1-phenyl-1,2-propanedione and other 1-aryl-2-alkyl-1,2-ethanediones, and cyclic alpha diketones. Suitable electron donor compounds include substituted amines, e.g., ethyl dimethylaminobenzoate or dimethylamino benzonitrile.

Suitable photoinitiators may also include phosphine oxides typically having a functional wavelength range of from about 380 nm to about 1200 nm. Examples of phosphine oxide free radical initiators with a functional wavelength range of from about 380 nm to about 450 nm include acyl and bisacyl phosphine oxides such as those described in U.S. Pat. Nos. 4,298,738, 4,324,744 and 4,385,109 and EP 0 173 567. Specific examples of the acylphosphine oxides include 2,4,6-trimethylbenzoyldiphenylphosphine oxide, bis(2,4,6-trimethylbenzoyl)phenylphosphine oxide, dibenzoylphenylphosphine oxide, bis(2,6-dimethoxybenzoyl)phenylphosphine oxide, tris(2,4-dimethylbenzoyl)phosphine oxide, tris(2-methoxybenzoyl)phosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, benzoyl-bis(2,6-dimethylphenyl) phosphonate, and 2,4,6-trimethylbenzoylethoxyphenylphosphine oxide. Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819), bis(2,6-dimethoxybenzoyl)-(2,4,4-trimethylpentyl) phosphine oxide (CGI 403), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700), a 1:1 mixture, by weight, of bis(2,4,6-trimethylbenzoyl)phenyl phosphine oxide and 2-hydroxy-2-methyl-1-phenylpropane-1-one (DAROCUR 4265), and ethyl 2,4,6-trimethylbenzylphenyl phosphinate (LUCIRIN LR8893X). Typically, the phosphine oxide initiator is present in the composition in catalytically effective amounts, such as from 0.1 percent by weight to 5.0 percent by weight, based on the total weight of the composition.

Tertiary amine reducing agents may be used in combination with an acylphosphine oxide Examples of suitable aromatic tertiary amine include N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, N,N-bis(2-hydroxyethyl)-3,5-dimethylaniline, N,N-bis(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, 4-N,N-dimethylaminobenzoic acid ethyl ester, 4-N,N-dimethylaminobenzoic acid methyl ester, 4-N,N-dimethylaminobenzoic acid n-butoxyethyl ester, 4-N,N-dimethylaminobenzoic acid 2-(methacryloyloxy) ethyl ester, 4-N,N-dimethylaminobenzophenone ethyl 4-(N,N-dimethylamino) benzoate and N,N-dimethylaminoethyl methacrylate. Examples of an aliphatic tertiary amine include trimethylamine, triethylamine, N-methyldiethanolamine, N-ethyldiethanolamine, N-n-butyldiethanolamine, N-lauryldiethanolamine, triethanolamine, 2-(dimethylamino) ethyl methacrylate, N-methyldiethanolamine dimethacrylate, N-ethyldiethanolamine dimethacrylate, triethanolamine monomethacrylate, triethanolamine dimethacrylate, and triethanolamine trimethacrylate.

The amine reducing agent may be present in the composition in an amount from 0.1 percent by weight to 5.0 percent by weight, based on the total weight of the composition.

The amount of active species of the polymerization initiator is not particularly limited. Suitably, the amount of polymerization initiator in the polymerization system according to (D) is in the range of from 0.001 to 5 mol % based on the total amount of the monomers.

The Cured Aqueous Dental Glass Ionomer Composition

The present aqueous dental glass ionomer composition is a curable dental composition, that is a cured dental glass ionomer composition/cement can be obtained therefrom by polymerizing the polymerizable polymer according to (B) and the monomer according to (C) in the presence of the reactive particulate glass (A) and the polymerization initiator system according to (D).

It was surprisingly found that when cured, the present dental glass ionomer composition has particularly advantageous mechanical properties:

Said composition's adhesive bond strength to dentin is of at least 5 MPa as measured according to ISO 29022: 2013; and
said composition's flexural strength is of at least 50 MPa as measured according to ISO 4049.

(E) The Non-Reactive Filler

The present aqueous dental glass ionomer composition may further comprise (E) a non-reactive filler, which do not undergo a cement reaction with the polyacid polymer.

Non-reactive fillers may be included in the present aqueous dental glass composition for changing the appearance of the composition, for controlling viscosity of the composition, for further improving mechanical strength of a dental glass ionomer cement obtained from the composition, and e.g. for imparting radiopacity. The non-reactive filler should be non-toxic and suitable for use in the mouth.

The filler may be in the form of an inorganic material. It can also be a crosslinked organic material that is insoluble in the polymerizable polymer according to (B) comprised in the present aqueous dental glass ionomer composition, and is optionally filled with inorganic filler.

For example, suitable non-reactive inorganic fillers may be quartz, nitrides such as silicon nitride, colloidal silica, submicron silica such as pyrogenic silicas, colloidal zirconia, feldspar, borosilicate glass, kaolin, talc or a metallic powder comprising one or more metals or metal alloys.

Examples of suitable non-reactive organic fillers include filled or unfilled particulate polycarbonates or polyepoxides. In embodiments, the surface of the non-reactive organic filler particles is treated with a coupling agent in order to enhance the bond between the filler and the matrix. Suitable coupling agents include silane compounds such as gamma-methacryloxypropyltrimethoxysilane, gamma-mercaptopropyltriethoxysilane and gamma-aminopropyltrimethoxysilane.

The non-reactive filler may have a unimodal or polymodal (e.g., bimodal) particle size distribution, wherein the particulate filler may have an average particle size of from 0.1 to 100 μm, such as from 1 to 40 μm. The particle size may be measured, for example, by electron microscopy or by using a conventional laser diffraction particle sizing method as embodied by a MALVERN Mastersizer S or MALVERN Mastersizer 2000 apparatus. The particulate filler may be a multimodal particulate non-reactive filler representing a mixture of two or more particulate fractions having different average particle sizes. The particulate reactive filler may also be a mixture of particles of different chemical composition. The particulate non-reactive filler may be surface modified by a surface modifying agent.

(F) The Polymerizable Crosslinker Having at Least Two Polymerizable C—C Double Bonds In embodiments, the aqueous dental glass ionomer composition according to the present disclosure further comprises:

(F) a polymerizable hydrolysis-stable crosslinker having at least two polymerizable carbon-carbon double bonds.

The crosslinker according to (F) may be an alkylenediol dimethylacrylate such as 1,3-butanediol dimethacrylate, 1,4-butanediol dimethacrylate, an alkylenediol divinyl ether such as 1,4-butanediol divinyl ether, di(ethylene glycol) dimethacrylate, di(ethylene glycol) divinyl ether, pentaerythritol diacrylate monostearate, ethylene glycol dimethacrylate, trimethylolpropane trimethacrylate, pentaerythritol triacrylate or triallyl ether, pentaerythritol tetraacrylate and trimethylolpropane triacrylate.

In embodiments, the crosslinker is a macromonomer of the following formula (6):

$$AX_n \qquad (6)$$

The macromonomer of formula (6) comprises a moiety A, and at least one substituent X.

In formula (6), A is a linear, branched or cyclic linker group containing at least n nitrogen atoms, whereby the linker group A has polyoxyalkylene and/or polyalkylene imine repeating units and optionally one or more acidic groups. The linker group A has a valency of at least one which corresponds to the total number of substituents X. Accordingly, linker group A may be monovalent (n=1), divalent (n=2), trivalent (n=3), tetravalent (n=4), pentavalent (n=5), or hexavalent (n=6). In embodiments, linker group A is divalent or trivalent, or it may be divalent.

In embodiments, the linker group A may be a linear or branched monomeric, oligomeric, polymeric or copolymeric group containing nitrogen atoms at the terminal positions for forming an amide bond with a moiety X. A monomeric groups is a low-molecular group having a molecular weight of up to 500. An oligomeric group is a group having a molecular weight of more than 500 to up to 10000 and may be prepared by a polymerization reaction. According to a further embodiment, the polymerizable compound of formula (6) contains one or more acidic groups selected from carboxylic acid groups, phosphonic acid groups, sulfonic acid groups or phosphoric acid ester groups.

In formula (6), X are moieties containing a polymerizable double bond and forming an amide bond with a nitrogen atom of A, which X may be the same or different and are represented by the following formula (7).

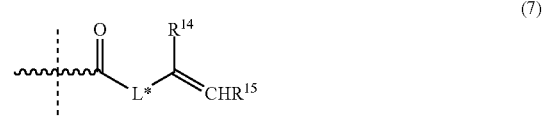

(7)

In formula (7), the dashed line indicates the attachment of X to the nitrogen atoms of at least two of the termini of formula (8).

In formula (7), $R^{14}$ and $R^{15}$ are independent from each other and represent a hydrogen atom, a linear $C_{1-6}$ or branched or cyclic $C_{3-8}$ alkyl group, or a group —$(CH_2)_m$—COOM, wherein M is a hydrogen atom or a metal atom and m is an integer of from 0 to 6. The metal atom may be an alkali metal atom or an alkaline earth metal. In case of an alkaline earth metal, the second charge on the metal atom is neutralized by either a further carboxylic acid anion or another anion. In embodiments, $R^{14}$ is a hydrogen atom or a methyl group, and $R^{15}$ may be a hydrogen atom or a group $-(CH_2)_m-COOH$, wherein m is 0, 1 or 2. In embodiments, $R^{15}$ is a hydrogen atom.

In formula (7), L* is a bond or a linear $C_{1-6}$ or branched or cyclic $C_{3-8}$ alkylene group, such as a single bond or a methylene or ethylene group. In embodiments, in formula (7), L* is a bond, that is the macromonomer of formula (6) is a (meth)acrylamide macromonomer.

In embodiments, in formula (6), n is an integer of at least one, such as 2 to 4, or 2.

In embodiments, in formula (6), A is a linker group represented by the following formula (8), wherein the nitrogen atom of at least two of the termini forms an amide bond with a substitutent X:

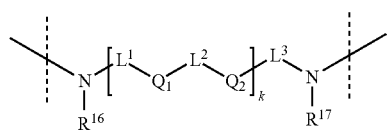
(8)

In formula (8), the dashed lines indicate the attachment of substituents X to the nitrogen atoms of at least two of the termini of formula (8).

In formula (8), $R^{16}$ and $R^{17}$ independently represent a hydrogen atom or a substituted or unsubstituted aliphatic or cycloaliphatic hydrocarbon group. Substituents of the aliphatic or cycloaliphatic hydrocarbon group may be selected from hydroxyl groups, thiol groups, amino groups, or carboxylic acid groups or a salt thereof. $R^{16}$ and $R^{17}$ may be the same or different. According to an embodiment, $R^{16}$ and $R^{17}$ independently represent a hydrogen atom, or a linear $C_{1-6}$ alkyl group or a branched or cyclic $C_{3-8}$ alkyl group, such as a linear $C_{1-3}$ or a branched $C_{3-5}$ alkyl group.

In formula (8), $L^1$, $L^2$, and $L^3$ may be the same or different. In case a plurality of $L^1$ an $L^2$ are present when k is at least 2, each of $L^1$ and $L^2$ may be the same or different. In embodiments, each of $L^1$ and each of the plurality $L^2$ are the same. $L^1$, $L^2$, and $L^3$ independently represent a single bond, or a linear $C_{2-20}$ or branched or cyclic $C_{3-20}$ hydrocarbon group containing from 1 to 6 heteroatoms selected from nitrogen and oxygen in the backbone of the hydrocarbon group, and optionally from 1 to 6 functional groups selected from carboxylic acid groups or a salt thereof, hydroxyl groups, thiol groups and amino groups. In a particular embodiment, $L_1$, $L_2$, and $L_3$ do not carry an optional functional group.

In embodiments, at least one, such as at least two of $L_1$, $L_2$, and $L_3$ do not represent a single bond. In embodiments, $L_1$, $L_2$, and $L_3$ contain 1 or 2 heteroatoms selected from nitrogen, and oxygen in the backbone of the hydrocarbon group. The hydrocarbon group may have 1 to 6 carbon atoms and may contain 1 or 2 heteroatoms selected from nitrogen, and oxygen in the backbone of the hydrocarbon group, and optionally from 1 to 3 carboxylic acid groups or a salt thereof.

In formula (8), $Q_1$ and $Q_2$, may be the same or different. $Q_1$ and $Q_2$ may represent a single bond or a linkage selected from an amide, a urethane, a urea and a thiourea linkage. In embodiments, at least one of $Q_1$ and $Q_2$ is not a single bond. In case $Q_1$ and $Q_2$ represent an amide or urethane linkage, the orientation of the amide or urethane linkage may be the same or different.

In formula (8), k is an integer of at least 0. When k is 0, then $L_3$ cannot be a single bond. In embodiments, k is in the range of from 0 to 60, such as from 1 to 40, or from 3 to 20, or from 5 to 10.

The linker group A imparts water solubility to the compound of formula (6). Water solubility within the sense of the present disclosure means that the compound of formula (6) can be dissolved as a 0.1 percent by weight solution in water at 25° C. In embodiments, the compound of formula (6) of the present disclosure has a water solubility of at least 2.0 weight % in water at 25° C.

In embodiments, the crosslinker in the form of the macromonomer of formula (6) is a (meth)acrylamide compound having the following structural formula:

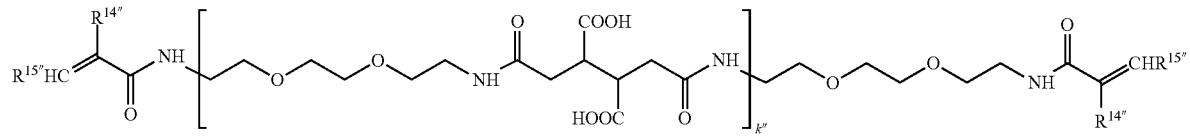

wherein
$R^{14''}$ is a hydrogen atom or a methyl group and
$R^{15''}$ is a hydrogen atom or a group $-(CH_2)_m-COOH$, wherein m is 0, 1 or 2, $R^{16''}$ and $R^{17''}$ may be a hydrogen atom, and
k" is from 3 to 20, such as from 5 to 10.

For example, the macromonomer of formula (6) is prepared by a process comprising (i) a step of a step-growth polymerization including a condensation reaction or addition reaction of a mixture containing a polyamine having a moiety of the formula (9) and additional hydrogen atoms, and a compound of the following formula (10) having at least two carboxylic acid groups, said carboxylic acid groups may be present in the form of an anhydride, in the presence of a compound of the following formula (11).

The polyamine of formula (9) has the following structural formula:

$$R^\alpha(NHR^\beta)_y \quad (9)$$

wherein
$R^\alpha$ represents an y-valent $C_{2-2o}$ straight-chain, branched or cyclic hydrocarbon group which may optionally contain from 1 to 6 heteroatoms selected from nitrogen, oxygen, or sulphur atoms in the backbone of the hydrocarbon group, and optionally from 1 to 6 functional groups selected from hydroxyl groups, thiol groups and amino groups;
$R^\beta$ represents a hydrogen atom or a substituted or unsubstituted aliphatic or cycloaliphatic hydrocarbon group; and
y represents an integer of at least 2.

The compound of formula (10) having at least two carboxylic acid groups has the following structural formula:

$$MOOC-R^\gamma-COOM \quad (10)$$

wherein $R^\gamma$ represents a linear $C_{1-20}$ or branched or cyclic $C_{3-20}$ or aromatic $C_{6-20}$ hydrocarbon group which may optionally contain from 1 to 6 heteroatoms selected from nitrogen, oxygen, or sulphur atoms in the backbone of the hydrocarbon group, and optionally from 1 to 6 functional groups selected from carboxylic acid groups, hydroxyl groups, thiol groups and amino groups, wherein the M which may be the same or different independently represent a hydrogen atom or a metal atom. The metal atom may be an alkali metal or an alkali earth metal. In case of an alkali earth metal, the additional charge on the metal may be neutralized by a further carboxylic acid anion or another anion present in the system.

The compound of formula (11) has the following structure:

$$Y^1-\overset{O}{C}-L^*-\overset{R^{16}}{C}=CHR^{17} \quad (11)$$

In compound of formula (11), $L^*$, $R^{16}$ and $R^{17}$ are defined as above, and $Y^1$ is a leaving group, for example a leaving group in the form of a chlorine or bromine atom, or $Y^1$ forms an intramolecular anhydride group together with a carboxylic acid group present in $R^{16}$ or $R^{17}$ and the adjacent carbonyl group.

The process further may further comprise a step (ii) of introducing the moieties of the formula (8) by reacting the polyamide obtained in step (i) with a compound of formula (11) wherein $Y^1$ is a leaving group and $R^{16}$ and $R^{17}$ are as defined above; or a step (iii) of reacting a mixture containing a polyamine and a compound of formula (11) for obtaining an amide.

The process may also comprise a step of a step-growth polymerization of a mixture containing the amide obtained in (iii) and a compound having at least two carboxylic acid groups or an anhydride thereof for obtaining the water-soluble polymerizable compound of the formula (1).

Furthermore, also disclosed is a crosslinker in the form of a polymerizable compound of the following formula (12), which is disclosed in patent publications EP2705827, WO2014040729 and in patent application EP 15 178 515:

$$A''-L(B)_{n'} \quad (12)$$

wherein
A" is a group of the following formula (13)

$$\left[ R^\bullet \overset{R^\blacktriangle}{\underset{R^\bullet}{\diagup}} X^{10}-N \right] \quad (13)$$

$X^{10}$ is CO, CS, $CH_2$, or a group $[X^{100}Z^{10}]_k$, wherein $X^{100}$ is an oxygen atom, a sulfur atom or NH, $Z^{10}$ is a linear $C_{1-4}$ or branched or cyclic $C_{3-6}$ alkylene group, and k is an integer of from 1 to 10;

$R^\blacklozenge$ is a hydrogen atom,
—COOM$^{10}$,
a linear $C_{1-16}$ or branched $C_{3-16}$ alkyl group which may be substituted with a $C_{3-6}$ cycloalkyl group, a $C_{6-14}$ aryl or $C_{3-14}$ heteroaryl group, —COOM$^{10}$, —PO$_3$M$^{10}$, —O—PO$_3$M$^{10}{}_2$ or —SO$_3$M$^{10}$,
a $C_{3-6}$cycloalkyl group which may be substituted with a $C_{1-16}$alkyl group, a $C_{6-14}$ aryl or $C_{3-14}$ heteroaryl group, —COOM$^{10}$, —PO$_3$M$^{10}$, —O—PO$_3$M$^{10}{}_2$ or —SO$_3$M$^{10}$,
a $C_{6-14}$ aryl or $C_{3-14}$ heteroaryl group which may be substituted with —COOM$^{10}$, —PO$_3$M$^{10}$, —O—PO$_3$M$^{10}{}_2$ or —SO$_3$M$^{10}$, $R^\bullet$ is a hydrogen atom,
—COOM$^{10}$
a linear $C_{1-16}$ or branched $C_{3-16}$ alkyl group which may be substituted with a $C_{6-14}$ aryl or $C_{3-14}$ heteroaryl group, —COOM$^{10}$, —PO$_3$M$^{10}$, —O—PO$_3$M$^{10}{}_2$ and —SO$_3$M$^{10}$,
a $C_{3-6}$cycloalkyl group which may be substituted with a $C_{1-16}$ alkyl group, a $C_{6-14}$ aryl or $C_{3-14}$ heteroaryl group, —COOM$^{10}$, —PO$_3$M$^{10}$, —O—PO$_3$M$^{10}{}_2$ or —SO$_3$M$^{10}$, or
a $C_{6-14}$ aryl or $C_{3-14}$ heteroaryl group which may be substituted with —COOM$^{10}$, —PO$_3$M$^{10}$, —O—PO$_3$M$^{10}{}_2$ and —SO$_3$M$^{10}$, $R^\blacktriangle$ is a hydrogen atom,
a linear $C_{1-16}$ or branched $C_{3-16}$ alkyl or linear $C_{2-16}$ or branched $C_{3-16}$ alkenyl group which may be substituted with a $C_{3-6}$cycloalkyl group, a $C_{6-14}$ aryl or $C_{3-14}$ heteroaryl group, —COOM$^{10}$, —PO$_3$M$^{10}$, —O—PO$_3$M$^{10}{}_2$ or —SO$_3$M$^{10}$, a $C_{3-6}$cycloalkyl or cycloalkenyl group which may be substituted with a $C_{1-16}$ alkyl group, a $C_{6-14}$ aryl or $C_{3-14}$ heteroaryl group, —COOM$^{10}$, —PO$_3$M$^{10}$, —O—PO$_3$M$^{10}{}_2$ or —SO$_3$M$^{10}$, a $C_{6-14}$ aryl group which may be substituted with —COOM$^{10}$, —PO$_3$M$^{10}$, —O—PO$_3$ M$^{10}{}_2$ or —SO$_3$M$^{10}$, for example $R^\blacktriangle$ is a linear $C_{1-10}$ or branched $C_{3-10}$ alkyl or linear $C_{2-10}$ or branched $C_{3-10}$ alkenyl group which may be substituted with a $C_{4-6}$ cycloalkyl group, a $C_{6-10}$ aryl or $C_{6-10}$ heteroaryl group, or $R^\blacktriangle$ may be a linear $C_{1-6}$ or branched $C_{3-6}$ alkyl or linear $C_{2-6}$ or branched $C_{3-6}$ alkenyl group which may be substituted with a $C_{6-10}$ aryl group, or $R^\blacktriangle$ may be a methyl group, an ethyl group, an allyl group or a benzyl group; and for example $R^\blacktriangle$ may be an ethyl group or an allyl group L is a single bond or a linker group;
B is selected from:
(i) a group according to the definition of A",
(ii) a group of the following formula (14)

$$\left[ R^{\blacklozenge'} \overset{R^{\blacktriangle'}}{\underset{R^{\bullet'}}{\diagup}} X^{10}-N \right] \quad (14)$$

wherein
$X^{20}$ independently has the same meaning as defined for $X^1$ in formula (13), R◆' and R●' are independent from each other and independently have the same meaning as defined for R◆ and R● in formula (13), R▲' is a hydrogen atom, a linear $C_{1-16}$ or branched $C_{3-16}$ alkyl group which may be substituted with a $C_{3-6}$ cycloalkyl group, a $C_{6-14}$ aryl or $C_{3-14}$ heteroaryl group, $—COOM^{10}$, $—PO_3M^{10}$, $—O—PO_3M^{10}{}_2$ or $—SO_3M^{10}$, a $C_{3-6}$ cycloalkyl group which may be substituted with a $C_{1-16}$ alkyl group, a $C_{6-14}$ aryl or $C_{3-14}$ heteroaryl group, $—COOM^{10}$, $—PO_3M^{10}$, $—O—PO_3M^{10}{}_2$ or $—SO_3M^{10}$, a $C_{6-14}$ aryl group which may be substituted with $—COOM^{10}$, $—PO_3M^{10}$, $—O—PO_3 M^{10}{}_2$ or $—SO_3M^{10}$, (iii) a group of the following formula (15)

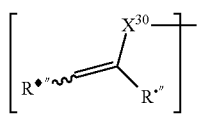

(15)

wherein $X^{30}$ is CO, $—CH_2CO—$, CS, or $—CH_2CS—$,

R◆'' and R●'' which are independent from each other and independently have the same meaning as defined for R◆ and R● in formula (13), or (iv) a group $[X^{40}Z^{200}]_pE$, wherein $Z^{200}$ is a linear $C_{1-4}$ or branched or cyclic $C_{3-6}$ alkylene group, $X^{40}$ is an oxygen atom, a sulfur atom or NH, E is a hydrogen atom, $PO_3M_2$, a linear $C_{1-16}$ or branched $C_{3-16}$ alkyl group which may be substituted with a $C_{3-6}$ cycloalkyl group, a $C_{6-14}$ aryl or $C_{3-14}$ heteroaryl group, $—COOM^{10}$, $—PO_3M^{10}$, $—O—PO_3M^{10}{}_2$ or $—SO_3M^{10}$, a $C_{3-6}$ cycloalkyl group which may be substituted with a $C_{1-16}$ alkyl group, a $C_{6-14}$ aryl or $C_{3-14}$ heteroaryl group, $—COOM^{10}$, $—PO_3M^{10}$, $—O—PO_3M^{10}{}_2$ or $—SO_3M^{10}$, a $C_{6-14}$ aryl or $C_{3-14}$ heteroaryl group which may be substituted with $—COOM^{10}$, $—PO_3M^{10}$, $—O—PO_3M^{10}{}_2$ or $—SO_3M^{10}$, and p is an integer of from 1 to 10;

and n' is an integer of from from 1 to 4;

wherein $M^{10}$ which are independent from each other each represent a hydrogen atom or a metal atom.

In formulae (13), (14) and (15), the jagged line indicates that R◆, R◆' and R◆'' may be in either the cis or trans orientation relative to $X^{10}$, $X^{20}$ or $X^{30}$.

In embodiments, when L is a single bond, B cannot be a group according to the definition of A'' or a group of the formula (13).

The following groups are exemplary of groups of formula (13), wherein M is a hydrogen atom or a metal atom:

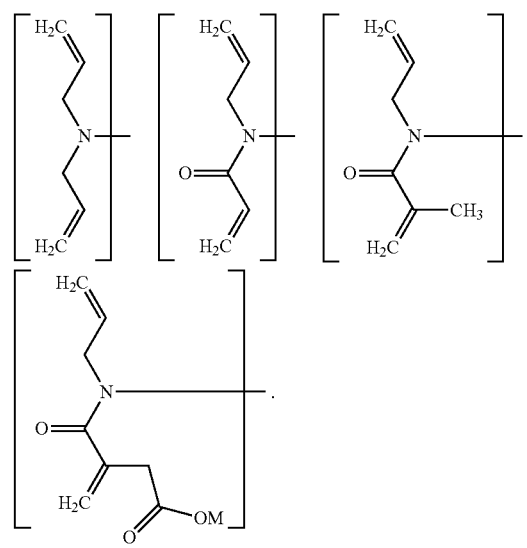

For L, the linker group may be a hydrocarbon group which may be aliphatic and/or aromatic and may have 1 to 45 carbon atoms. The hydrocarbon group may be substituted with from 1 to 6 $C_{1-4}$ alkyl groups. Specific examples of the alkyl groups are methyl, ethyl, n-propyl, propyl, n-butyl, i-butyl or tert.-butyl. In one embodiment, for L, the hydrocarbon group of the linker group may contain from 1 to 5 heteroatoms selected from oxygen, nitrogen and sulphur. The oxygen atoms and sulphur atoms in the hydrocarbon group may be in the form of ether or thioether bonds, keto or sulfoxide groups, carboxylic acid or ester groups, sulfonic acid or ester groups, hydroxyl groups and thiol or thioester groups. In case of an aliphatic group, L may be a linear $C_1$ to $C_{18}$ or branched $C_3$ to $C_{18}$ alkylene group, linear $C_2$ to $C_{18}$ or branched $C_3$ to $C_{18}$ alkenylene group, $C_3$ to $C_{18}$ cycloalkylene or cycloalkenylene group. In case of an aromatic group, L may be a $C_6$ to $C_{18}$ arylene or heteroarylene group. Specifically, L may be a divalent substituted or unsubstituted linear $C_1$ to $C_{20}$ or branched $C_3$ to $C_{20}$ alkylene or linear $C_2$ to $C_{20}$ or branched $C_3$ to $C_{20}$ alkenylene group, substituted or unsubstituted $C_{6-14}$ arylene group, substituted or unsubstituted $C_3$ to $C_{20}$ cycloalkylene group, substituted or unsubstituted $C_7$ to $C_{20}$ arylenealkylene group.

According to one embodiment, L represents a saturated or unsaturated aliphatic $C_{2-20}$ hydrocarbon chain which may contain 2 to 4 oxygen atoms or nitrogen atoms, and which may be substituted with 1 to 6 linear $C_{1-4}$ or branched or cyclic $C_{3-6}$ alkyl groups, or L may be a substituted or unsubstituted $C_7$ to $C_{20}$ arylenealkylene group which may be substituted with 1 to 6 linear $C_{1-4}$ or branched or cyclic $C_{3-6}$ alkyl groups.

In embodiments, the linker group is a divalent $C_{1-12}$ hydrocarbon group. The divalent $C_{1-12}$ hydrocarbon group may contain 1 to 3 carbonyl groups or heteroatoms selected from oxygen, nitrogen and sulfur. Moreover, the $C_{1-12}$ hydrocarbon group may be substituted with a hydroxyl group, a $C_{6-14}$ aryl group, $—COOM$, $—PO_3M$, $—O—PO_3M_2$ or $—SO_3M$, wherein M is a hydrogen atom or a metal atom. Specific examples of a divalent $C_{1-12}$ hydrocarbon group are a linear $C_{1-12}$ or branched $C_{3-12}$ alkylene group such as a methylene, ethylene, propylene or butylene group, and linear $C_{2-12}$ or branched $C_{3-12}$ alkenylene group such as a ethenylene, propenylene or butenylene group, which groups may be substituted with a hydroxyl group, a $C_{6-14}$ aryl group, —COOM, —$PO_3M$, —O—$PO_3M_2$ or —$SO_3M$.

Exemplary divalent linker groups may be selected from methylene, ethylene, propylene, butylene, ethenylene, propenylene (prop-1-enylene or prop-2-enylene) or butenylene (but-1-enylene, but-2-enylene) and the following divalent groups:

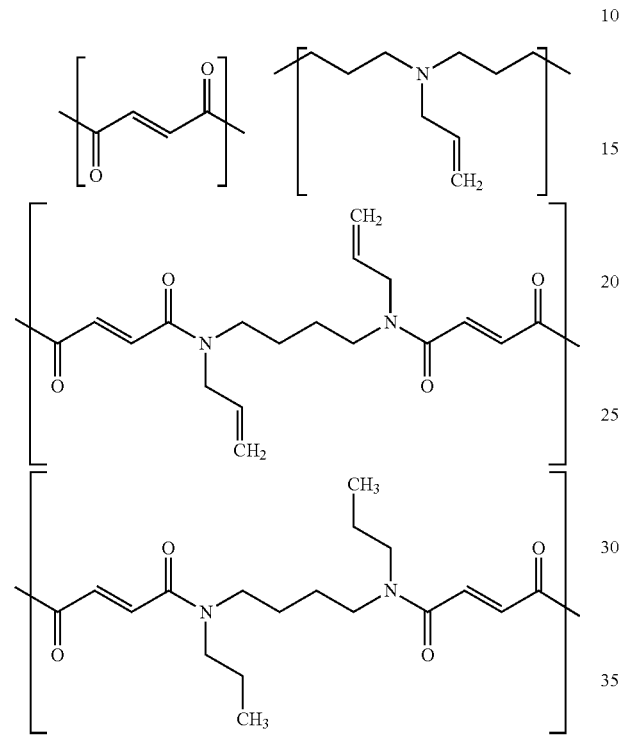

In embodiments, in the crosslinker of formula (12), $X^{10}$ is CO, that is, the crosslinker is a (meth)acrylamide compound.

In further embodiments, the crosslinker of formula (12) is selected from the group consisting of 1,3-bisacrylamido-propan (BAP), 1,3-bisacrylamido-2-ethyl-propan (BAPEN), N,N-di(allyl acrylamido) propane and compounds having the following structural formulae:

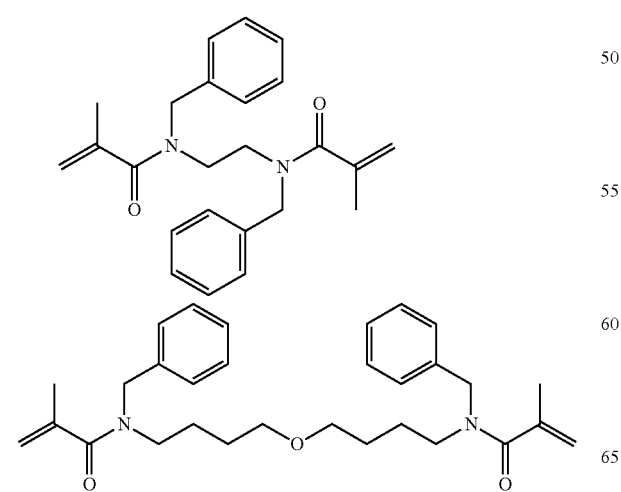

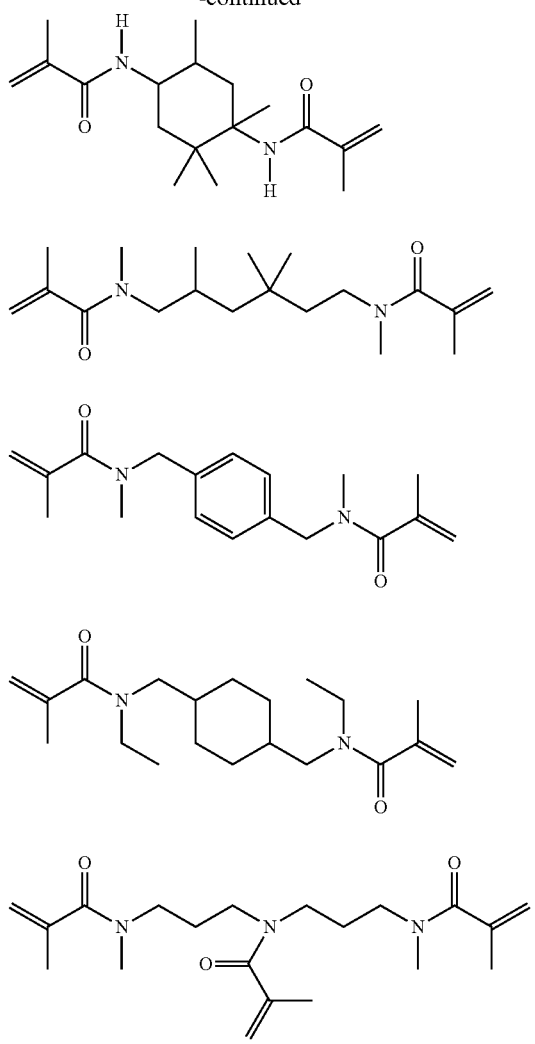

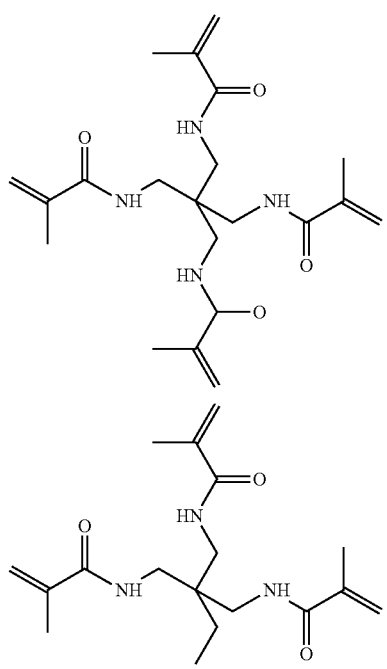

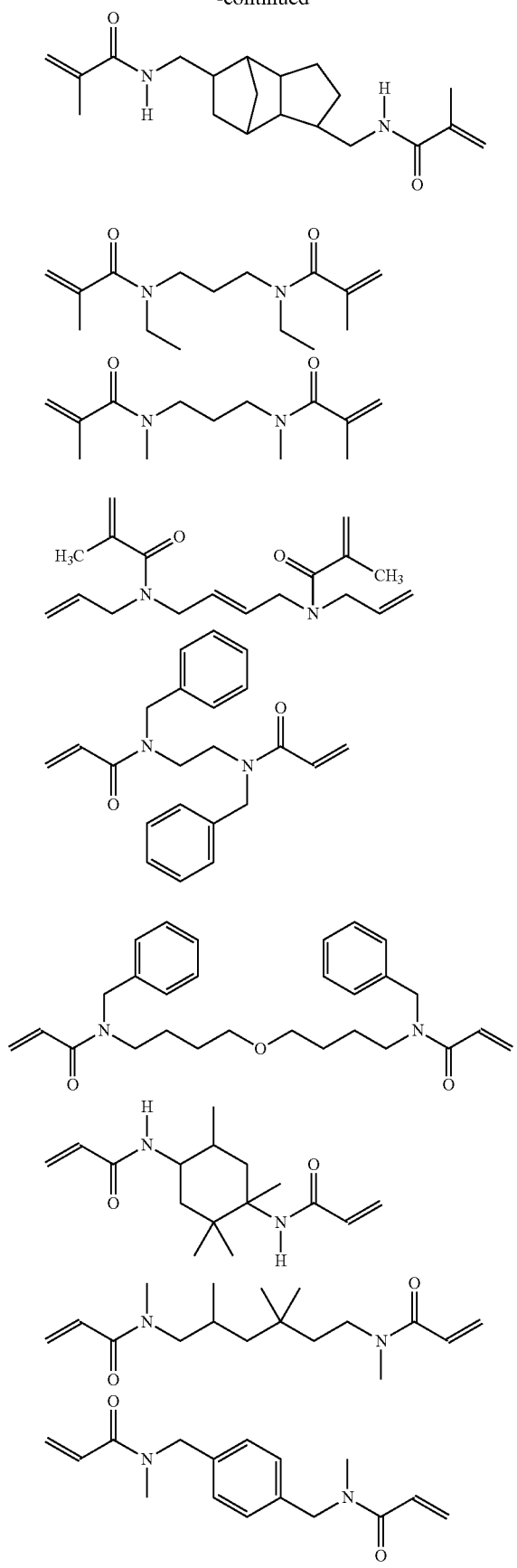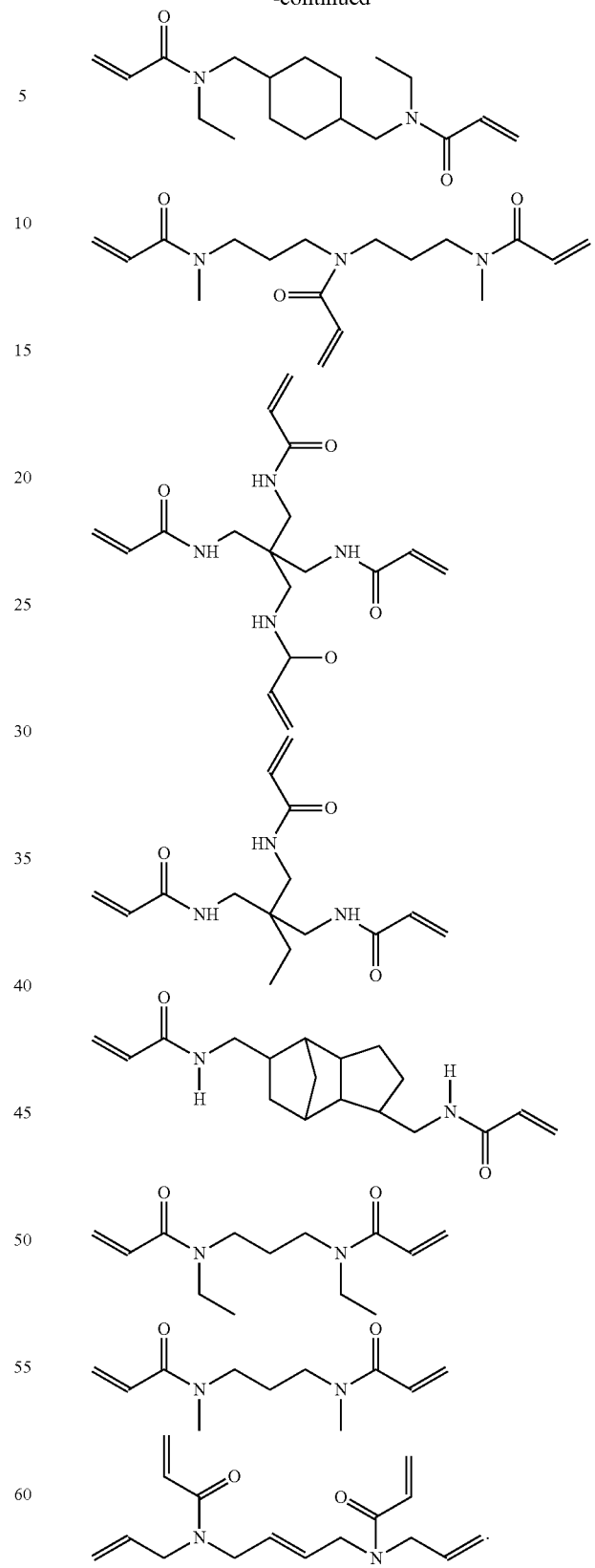
In yet further embodiments, the crosslinker of formula (12) is selected from the group consisting of N,N'-(2E)-but-2-en-1,4-diallylbis-[(N-prop-2-en-1) amide (BAABE), N,N'-diethyl-1,3-bisacrylamido-propan (BADEP), 1,3-bisacrylamido-propan (BAP), 1,3-bisacrylamido-2-ethyl-propan (BAPEN) and N,N-di(allyl acrylamido) propane. For example, compound of formula (12) may be N,N'-(2E)-but-2-en-1,4-diallylbis-[(N-prop-2-en-1) amide (BAABE) or N,N'-diethyl-1,3-bisacrylamido-propan (BADEP).

In embodiments, the aqueous dental glass ionomer composition according to the present disclosure comprises a combination of one or more crosslinkers of formula (7) and one or more crosslinkers of formula (12).

In embodiments, the polymerizable hydrolysis-stable crosslinker according to (F) is contained in an amount of up to 30 percent by weight, such as from 5 to 20 percent by weight, or from 8 to 15 percent by weight based on the total weight of the aqueous dental glass ionomer composition.

Further Optional Components

The aqueous dental glass ionomer composition according to the present disclosure may, besides of optional components (E) and (F), comprise additional optional components.

However, in embodiments, the aqueous dental glass ionomer composition does not comprise a non-polymerizable polymer having no polymerizable carbon-carbon double bond (s).

For example, as additional optional components, the aqueous dental glass ionomer composition according to the present disclosure may also include further components to improve the radio-opacity, such as $CaWO_4$, $ZrO_2$, $YF_3$ or to increase the fluoride release such as $YF_3$.

Further, the aqueous dental glass ionomer composition according to the present disclosure may also include a modifying agent such as tartaric acid. Such modifying agent provides for adjusting the working time and a setting time of the glass ionomer cement reaction, respectively, when preparing the cement as described in U.S. Pat. Nos. 4,089,830, 4,209,434, 4,317,681 and 4,374,936. In general, an increase in working time results in an increase in setting time as well.

The "working time" is the time between the beginning of the setting reaction when the polymer and modified particulate reactive filler are combined in the presence of water, and the time the setting reaction proceeds to the point when it is no longer practical to perform further physical work upon the system, e.g. spatulate it or reshape it, for its intended dental or medical application.

The "setting time" is the time measured from the beginning of the setting reaction in a restoration to the time sufficient hardening has occurred to allow subsequent clinical or surgical procedures to be performed on the surface of the restoration.

In a setting reaction, due to the presence of polymerizable double bonds, a polymerization reaction takes place.

The aqueous dental glass ionomer composition according to the present disclosure may contain further components such as solvents, pigments, nonvitreous fillers, free radical scavengers, polymerization inhibitors, reactive and nonreactive diluents e.g. surfactants (such as to enhance solubility of an inhibitor e. g., polyoxyethylene), coupling agents to enhance reactivity of fillers e.g., 3-(trimethoxysilyl) propyl methacrylate, and rheology modifiers.

Suitable solvents or nonreactive diluents include alcohols such as ethanol and propanol.

Suitable reactive diluents are alpha,beta unsaturated monomers for providing altered properties such as toughness, adhesion, and set time. Such alpha,beta-unsaturated monomers may be acrylates and methacrylates such as methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate (HEMA), hydroxypropyl acrylate, hydroxypropyl methacrylate, tetrahydrofurfuryl acrylate, tetrahydrofurfuryl methacrylate, glycidyl acrylate, glycidyl methacrylate, 2-propenoic acid 2-methyl 1,1'-[(1-methylethylidene)bis[4,1-phenyleneoxy(2-hydroxy-3,1-propanediyl)]]ester also termed bisphenol A glycerolate dimethacrylate ("bis-GMA", CAS-No. 1565-94-2), glycerol mono- and di-acrylate, glycerol mono- and di-methacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30 especially triethylene glycol dimethacrylate ("TEGDMA"), neopentyl glycol diacrylate, neopentylglycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexanediol diacrylate, 1,6-hexanediol dimethacrylate, di-2-methacryloyloxyethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethyl-hexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-metha-cryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl-4-cyclohexyl carbamate, 2,2'-bis (4-methacryloxyphenyl)propane, 2,2'bis(4-acryloxyphenyl) propane, 2,2'-bis[4(2-hydroxy-3-methacryloxy-phenyl)] propane, 2,2'-bis[4(2-hydroxy-3-acryloxy-phenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl) propane, 2,2'-bis(4-acryloxydiethoxyphenyl)propane, 2,2'-bis[3(4-phenoxy)-2-hydroxypropane-1-methacrylate] propane, and 2,2'-bis[3(4-phenoxy)-2-hydroxypropane-1-acrylate]propane, may be mentioned. Other suitable examples of polymerizable components are isopropenyl oxazoline, vinyl azolactone, vinyl pyrrolidone, styrene, divinylbenzene, urethane acrylates or methacrylates, epoxy acrylates or methacrylates and polyol acrylates or methacrylates. Mixtures of alpha,beta-unsaturated monomers can be added if desired. In embodiments, the mixed but unset dental compositions of the disclosure will contain a combined weight of from about 0.5 to about 40%, such as from about 1 to about 30% or such as from about 5 to 20% water, solvents, diluents and alpha,beta-unsaturated monomers, based on the total weight (including such water, solvents, diluents and alpha,beta-unsaturated monomers) of the mixed but unset aqueous dental glass ionomer composition components.

Example of suitable free radical scavengers are 4-methoxyphenol, phenyl-N-tert-butylnitrone (PBN) and phenothiazine. An example of a suitable inhibitor is tert.-butyl hydroquinone (TBHQ), hydroxytoluene or butylated hydroxytoluene (BHT). The amount of inhibitor may be selected from 0.001 to 2%, such as from 0.02 to 0.5% based on the total weight of the polymerizable polymer according to (B)/monomer according to (C)/water mixture.

Nanoparticles

Any particulate components of the present aqueous dental glass ionomer composition, such as the above described reactive particulate glass (A), non-reactive filler (E) or particulate further optional components may be in the form of nanoparticles.

The nanoparticles may be uniformly dispersed in the aqueous dental glass ionomer composition.

The nanoparticles may have an unimodal or polymodal (e.g., bimodal) particle size distribution.

In embodiments, the particles have diameters from 2 nm to 20 μm, such as from 2 nm to 200 nm.

In embodiments, the aqueous dental glass ionomer composition comprises up to 80 percent by weight of dispersed nanoparticles, such as up to 75 percent based on the total weight of the composition.

Embodiments of the Aqueous Dental Glass Ionomer Composition

According to one embodiment, the aqueous dental glass ionomer composition according to the disclosure comprises
(A) a reactive particulate glass comprising
1) 20 to 45% by weight of silica,
2) 20 to 40% by weight of alumina,
3) 20 to 40% by weight of strontium oxide,
4) 1 to 10% by weight of $P_2O_5$, and
5) 3 to 25% by weight of fluoride,
(B) a water-soluble, polymerizable polymer comprising acidic groups, which is reactive with the particulate glass in a cement reaction, whereby the polymerizable polymer has a polymer backbone and hydrolysis-stable pendant groups having one or more polymerizable carbon-carbon double bonds, wherein the polymerizable polymer is obtainable by a process comprising
a) a step of polymerizing a mixture comprising
(i) a first polymerizable monomer represented by the general formula (1):

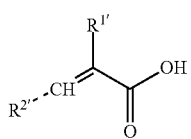

(1')

wherein
$R^{1'}$ is a hydrogen atom, or a linear $C_{1-4}$ or branched or cyclic $C_{3-6}$ alkyl group which may be substituted with a —COOH group, $R^{2'}$ is a hydrogen atom, or a linear $C_{1-4}$ or branched or cyclic $C_{3-6}$ group which may be substituted with a —COOH group,
for example $R^{1'}$ and $R^{2'}$ may be selected with the proviso that the molecular weight of the first polymerizable monomer is at most 200 Da, such as at most 150 Da;
the compound of formula (1') may be selected from the group consisting of itaconic acid, (meth)acrylic acid, maleic acid or an anhydride thereof, the compound of formula (1') may be (meth)acrylic acid or the intramolecular anhydride of itaconic acid or maleic acid, or the compound of formula (1') may be acrylic acid or the intramolecular anhydride of itaconic acid, and optionally
(ii) a second copolymerizable monomer represented by the general formula (2'):

wherein
$R^{3'}$ is a hydrogen atom;
X' is a protected hydroxyl or amino group or a hydrocarbon group having 1 to 6 carbon atoms, which is substituted with a hydroxyl and/or amino group which may carry a protecting group which hydrocarbon group may further be substituted with a —COOH group;
Y' is a hydrogen atom, a —COOH group or a hydrocarbon group having 1 to 6 carbon atoms, which hydrocarbon group may further be substituted with a —COOH group;
for obtaining a water-soluble polymer;
b) a step of coupling to the water-soluble polymer a compound having a polymerizable moiety and a functional group represented by the general formulae (3') and (4'):

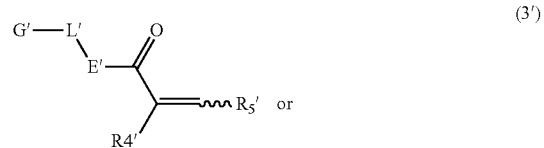

wherein in formula (3')
G' is a hydroxyl group or an amino group, which group may carry a protecting group;
E' is an oxygen atom or a secondary amine group (—NH—), in embodiments, G and E are selected such that G is an optionally protected hydroxyl group and E is an oxygen atom, or G is an optionally protected amino group and E is a secondary amino group (NH) or a tertiary amino group NR$^\#$ wherein R$^\#$ is a linear C$_{1-4}$ or branched or cyclic C$_{3-6}$ alkyl group;

R$^{4'}$ is a hydrogen atom or a methyl group;

R$^{5'}$ is a hydrogen atom or a methyl group;

L' is a —[C$_{1-5}$ alkylene-Het]$_n$(C$_{1-4}$ alkylene)- group wherein Het is a nitrogen or an oxygen atom and with n=0 to 3, for example L may be linear C$_{1-5}$ or branched C$_{3-5}$ alkylene, in formula (4'), G$^\#$ is —N=C=O or —CO-LG wherein LG is a leaving group or wherein LG may replace Z''' and form with R$^6$ or R$^7$ an intramolecular carboxylic acid anhydride group, or wherein two molecules of formula (4) form an intermolecular carboxylic acid anhydride group by condensation of LG and/or —COOZ''', wherein LG is an oxygen atom;

A$^\#$ is a single bond, a linear C$_{1-6}$ or a branched or cyclic C$_{3-8}$ alkylene group or a —CO—[Het-C$_{1-5}$ alkylene]$_n$- group wherein Het is a secondary amino group (NH) or an oxygen atom with n=1 to 3;

R$^{7'}$ is a hydrogen atom or a hydrocarbon group having 1 to 3 carbon atoms which may be substituted with a —COOH group, the compound of formula (4') may be itaconic acid, (meth)acrylic acid, maleic acid or an anhydride of the aforementioned acids formed of two identical or different acids, the compound of formula (4') may be (meth) acrylic acid or an intermolecular anhydride thereof or an intramolecular anhydride of itaconic acid or maleic acid, or the compound of formula (4') may be the intramolecular anhydride of itaconic acid, wherein the optionally protected carboxyl acid groups and the optionally protected hydroxyl groups are deprotected, so that polymerizable pendant groups are linked to the backbone by ester or urethane groups, and, optionally, a step of deprotecting the protected carboxylic acid group after step a) or step b), for obtaining a polymerizable polymer having an average molecular weight M$_w$ in the range of from 3·10$^4$ to 2·5·10$^5$ Da;

(C) a hydrolysis-stable, water soluble monomer having a single polymerizable double bond in the form of a (meth)acrylamide monomer represented by the general formula

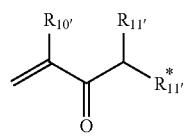

(5'')

wherein

R$_{10'}$ represents a hydrogen atom, a linear C$_{1-8}$ or branched C$_{3-8}$ alkyl group which may be substituted with a C$_{4-6}$ cycloalkyl group, a C$_{6-10}$ aryl, a C$_{4-10}$ heteroaryl group, a C$_{4-6}$ cycloalkyl group which may be substituted with a C$_{1-6}$ alkyl group, a C$_{6-10}$ aryl or C$_{4-10}$ heteroaryl group, or a C$_{6-10}$ aryl group;

R$_{11'}$ and R*$_{11'}$ independently represent a hydrogen atom, a linear C$_{1-10}$ or branched C$_{3-10}$ alkyl group which may be substituted with a phenyl group or —OH, or a C$_{4-8}$ cycloalkyl group, or R$_{11'}$ and R*$_{11'}$ cooperatively form a N-piperidinyl or N-morpholinyl ring; or R$_{11'}$ and R*$_{11'}$ independently represent a methyl or ethyl group, m' is an integer in the range from 1 to 10, and (D) a polymerization initiator system being based on a radical initiator in the form of a photoinitiator or a redox initiator or a mixture thereof.

In one embodiment, the first polymerizable monomer may be represented by the general formula (1/1'), the second copolymerizable monomer represented by the general formula (2/2'), the compound having a polymerizable moiety and a functional group reactive with an amino group of repeating units derived from the second copolymerizable monomer represented by the general formula (3/3') and the hydrolysis-stable, water-soluble macromonomer having one polymerizable double bond represented by the general formula (4/4') as follows:

the first polymerizable monomer:

is an optionally protected (meth)acrylic acid monomer, such as tert-butylacrylate or benzyl (meth)acrylate, (meth)acrylic acid, (meth)acrylic acid anhydride, the intermolecular anhydride of itaconic acid or maleic acid, the first polymerizable monomer may be acrylic acid and the intermolecular anhydride of itaconic acid;

the second copolymerizable monomer:

is represented by the general formula (2''):

(2'')

wherein

R$^{3''}$ is a hydrogen atom;

X'' is a protected hydroxyl or amino group or a hydrocarbon group having 1 to 3 carbon atoms, which is substituted with a hydroxyl and/or amino group which may carry a protecting group, which hydrocarbon group may contain an amide bond and which hydrocarbon group may further be substituted with a —COOH group;

Y'' is a hydrogen atom, a —COOH group or a hydrocarbon group having 1 to 3 carbon atoms, which hydrocarbon group may further be substituted with a —COOH group;

the compound having a polymerizable moiety and a functional group reactive with a carboxylic acid group of repeating units derived from the first polymerizable monomer is represented by the general formula (3''):

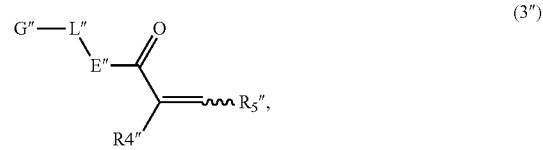

(3'')

wherein

G'' is a hydroxyl or amino group;

E'' is an oxygen atom or a secondary amine group (—NH—);

ably G and E are selected such that G is an optionally protected hydroxyl group and E is an oxygen atom, or G is an optionally protected amino group and E is a secondary amino group (NH);

$R^{4''}$ is a hydrogen atom or a methyl group;

$R^{5''}$ is a hydrogen atom;

L" $C_{1-3}$ alkylene, such as methylene or ethylene, the compound of formula (3) may be selected from the group consisting of 3-hydroxypropyl acrylate, 3-hydroxypropyl methacrylate, 2-hydroxyethyl acrylate, 2-hydroxyethyl methacrylate (HEMA), or a C1-6 alkyl ether thereof, the compound of formula (3) may be 2-hydroxyethyl acrylate or 2-hydroxyethyl methacrylate (HEMA); and the compound having a polymerizable moiety and a functional group reactive with an optionally protected hydroxyl and/or amino group of repeating units derived from the second copolymerizable monomer:

is represented by the general formula (4"),

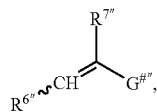

(4")

wherein in formula (4'), $G^{\#}$ is —N=C=O or —COOH;

$A^{\#}$ is a single bond, a methylene or ethylene group or a —CO-Het-$C_{1-3}$ alkylene group;

$R^{6''}$ is a hydrogen atom;

$R^{7''}$ is a hydrogen atom or a hydrocarbon group having 1 to 3 carbon atoms which may be substituted with a —COOH group, the compound of formula (4") may be itaconic acid, (meth)acrylic acid, maleic acid or an anhydride of the aforementioned acids formed of two identical or different acids, such as (meth) acrylic acid or anhydride, or an intramolecular anhydride of itaconic acid or maleic acid, or such as acrylic acid or the intramolecular anhydride of itaconic acid;

the hydrolysis-stable, water-soluble monomer having a single polymerizable double bond in the form of a (meth)acrylamide monomer represented by the general formula (5''')

wherein $R_{10}''$ represents a hydrogen atom, a linear $C_{1-4}$ or branched $C_{3-6}$ alkyl group which may be substituted with a cyclohexyl group or a phenyl group, or a $C_{3-8}$ cycloalkyl group which may be substituted with a linear $C_{1-4}$ or branched $C_{3-5}$ alkyl group, for example, $R_{10}$ represents a hydrogen atom or a linear $C_{1-3}$ or branched $C_{3-5}$ alkyl group;

$R_{11}''$ and $R^*_{11}''$ independently represent a hydrogen atom, a linear $C_{1-10}$ or branched $C_{3-10}$ alkyl group which may be substituted with a $C_{6-10}$ aryl group or —OH, a cyclic $C_{3-10}$ alkyl group, or $R_{11}''$ and $R^*_{11}''$ cooperatively form a N-piperidinyl or N-morpholinyl ring; more preferably a linear $C_{1-4}$ or branched $C_{3-6}$ alkyl group which may be substituted with —OH, and most preferably a methyl or ethyl group, compound of formula (5''') is selected from the group consisting of

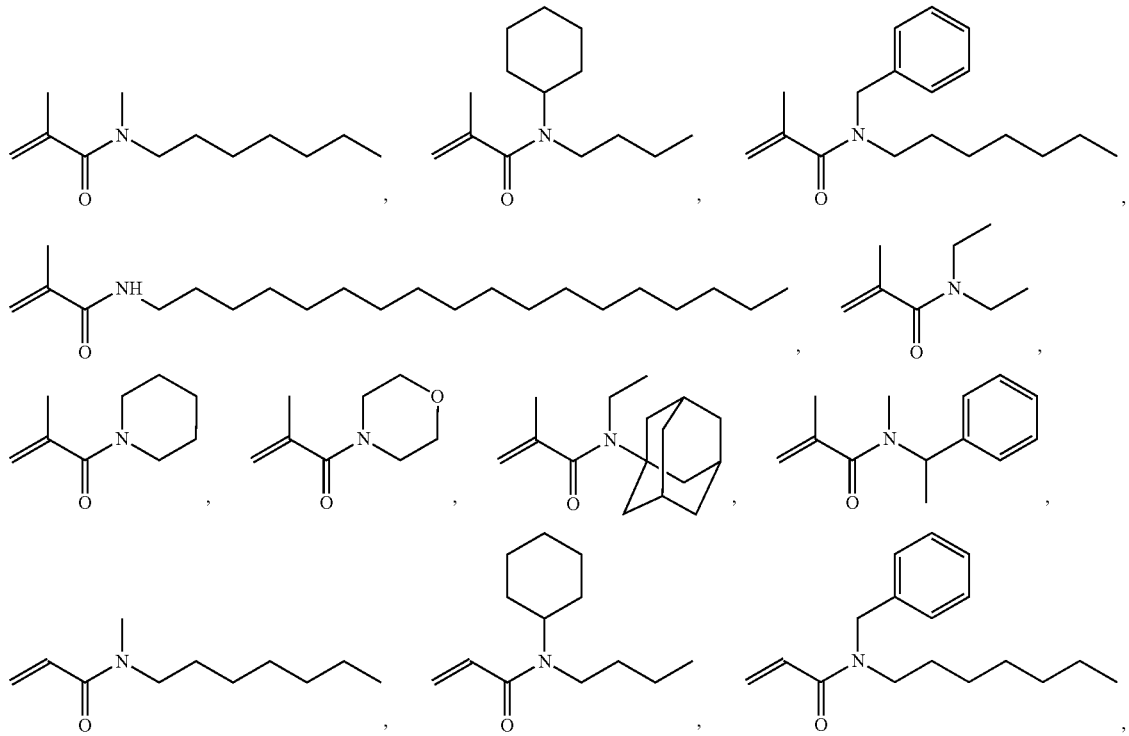

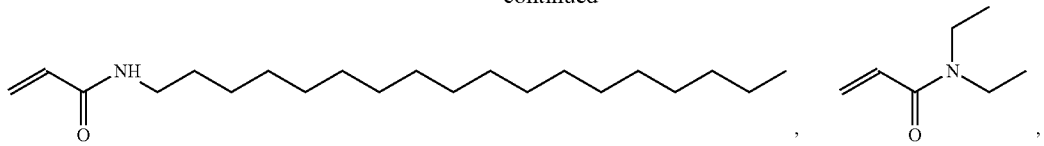

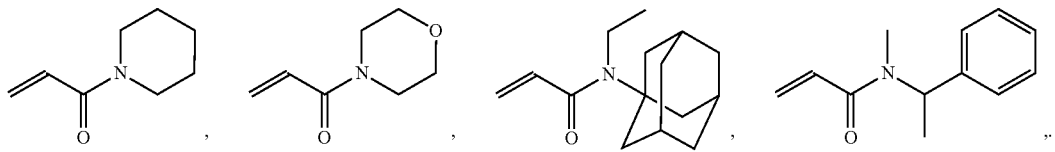

2-hydroxyethyl acrylamide (HEAA), N,N-dimethyl(meth)acrylamide, N,N-di-n-propyl(meth)acrylamide, and N-ethyl-N-methyl(meth)acrylamide, most preferably compound of formula (6") is selected from the group consisting of 2-hydroxyethyl acrylamide (HEAA), N,N-dimethyl(meth)acrylamide, N,N-diethyl(meth)acrylamide, N,N-di-n-propyl(meth)acrylamide, and N-ethyl-N-methyl(meth)acrylamide.

In the last mentioned embodiment, the polymerizable polymer obtained in step b) has one of the following structures:

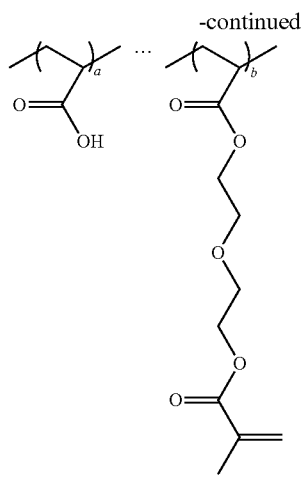

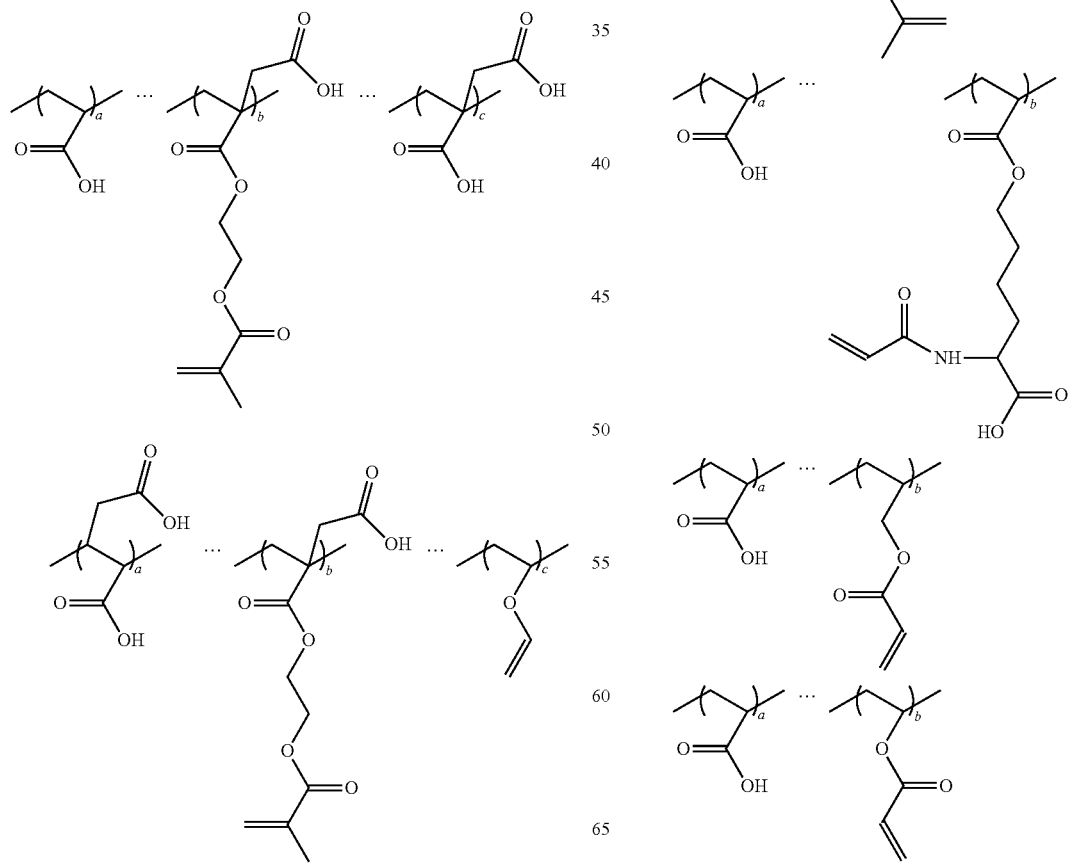

-continued

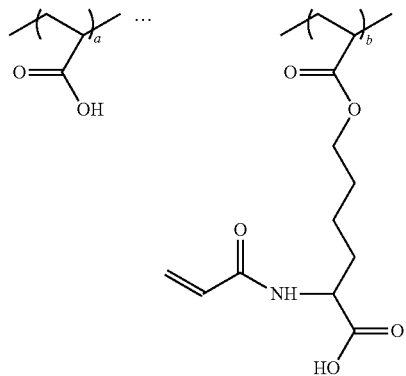

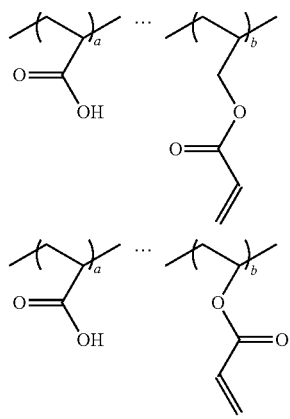

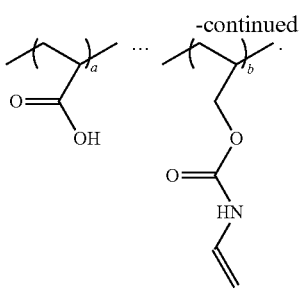

The Use of a Mixture Comprising an Aqueous Dental Glass Ionomer Composition Comprising Components (A), (B) and (C)

A composition comprising at least (A) a reactive particulate glass, (B) a water-soluble, polymerizable polymer comprising acidic groups, which is reactive with the particulate glass in a cement reaction, and (C) a hydrolysis-stable, water-soluble monomer having a single polymerizable double bond and optionally a carboxylic acid group or hydroxyl group may be used for the preparation of an aqueous dental glass ionomer composition.

For this use, the compounds of formula (1) and optionally (2), the compounds (3) or (4) and compound of formula (5) as described above may be used for the preparation of an aqueous dental glass ionomer composition. In embodiments, the compounds of formula (1) and optionally (2), the compounds (3) or (4) and compound of formula (5) are used alone or in combination with at least one of (D) the polymerization initiator system, (E) the non-reactive filler, (F) the crosslinker and the further optional components as described above for the preparation of a dental composition.

The Process for the Preparation an Aqueous Dental Glass Ionomer Composition

The above described aqueous dental glass ionomer composition may be provided by the process defined in any one of claims 13 to 15.

The process is not specifically limited. For example, the water-soluble polymer is selected from a polyacid and a polyanhydride, wherein the polyacid may be branched and/or hyperbranched.

In the process for the preparation an aqueous dental glass ionomer composition, it is preferred that the step b) of coupling to the water-soluble polymer comprises activation of the water-soluble polymer. In embodiments, the activation of the water-soluble polymer provides a polyacid halogenide, such as a polyacid chloride or bromide.

The water-soluble polymer may be a cyclopolymer. In embodiments, the cyclopolymer is provided by polymerizing a mixture comprising divinyl ether and maleic anhydride, or a mixture comprising (meth)acrylic acid and itaconic anhydride. For example, the cyclopolymer may be provided by polymerizing a mixture comprising acrylic acid and itaconic anhydride.

In embodiments, in step b), the functional group reactive with an optionally protected carboxylic acid group of repeating units derived from the first polymerizable monomer is a group —OR' wherein R' is a hydrogen atom, or a linear $C_{1-6}$ or branched or cyclic $C_{3-6}$ alkyl group, and/or the functional group reactive with an optionally protected hydroxyl and/or amino group of repeating units derived from the second copolymerizable monomer is an isocyanate group or a —CO-LG' group wherein LG' denotes a leaving group being a chlorine atom, a bromine atom, or forms with the adjacent carbonyl group a carboxylic acid anhydride moiety. In embodiments, in step b), the functional group reactive with an optionally protected carboxylic acid group of repeating units derived from the first polymerizable monomer is coupled to a compound of formula (3), and/or the functional group reactive with an optionally protected hydroxyl and/or amino group of repeating units derived from the second copolymerizable monomer is coupled to a compound of formula (4).

The disclosure will now be further illustrated by the following Examples.

Examples

Preparation of (B) the Water-Soluble, Polymerizable Polymer Comprising Acidic Groups By way of example, for component (B) of the present aqueous dental glass ionomer composition, poly(acrylic acid-co-itaconic anhydride) coupled with 2-hydroxyethyl methacrylate (PAA-IAA-HEMA) was prepared by the following two-step synthesis:

Step 1: Poly(Acrylic Acid-Co-Itaconic Anhydride) (PAA-IAA)

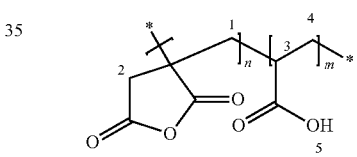

In a 100 mL two-neck bottle, equipped with a septum and reflux condenser, 9.5 mL (139 mmol) acrylic acid (AA) are placed and 22.4 mL (33 wt.-%) distilled ethyl acetate or alternatively 22.4 mL 1,4-dioxane are added. 0.3-15.6 g (2.8-139 mmol) itaconic acid anhydride (IAA) solved in 0.7-36.4 distilled ethyl acetate (or dioxane) as well as 230-456 mg (1 mol-%) azoisobutyronitrile (AIBN) are added and the clear solution is gently purged with nitrogen for 30 minutes. The polymerization is initiated by heating the mixture up to 70° C. (oil bath) for 4 h. During the whole reaction a nitrogen blanket is kept over the liquid. The precipitate from the polymerization in ethyl acetate is collected via filtration and reprecipitated from 20 mL 1,4 dioxane in 200 mL acetonitrile.

The polymer from the solution-polymerization in dioxane is collected via precipitation in a 10-fold excess of acetonitrile.

In both cases, the obtained, colorless solid is dried under reduced pressure at 50° C.

$^1$H-NMR (300 MHz, DMSO-$d_6$): δ [ppm]=12.3 (br, 5), 3.4 (br, 2), 2.2 (br, 3), 1.7 (br, 1 and 4).

GPC (water): averaged $M_n$=2.900-3.600 g/mol, averaged $M_w$=15,000-47,400 g/mol, D=5.1-14.6

DSC: $T_g$=64° C. (AA:IAA=1:1) −96° C. (AA:IAA=50:1)

Step 2: Polymer Analogue Modification of Poly(Acrylic Acid-Co-Itaconic Anhydride) with 2-Hydroxyethyl Methacrylate (PAA-IAA-HEMA)

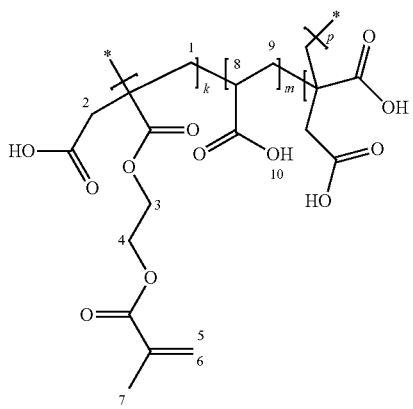

In a 10 mL round-bottom flask, 0.5 g (5.5 mmol) poly(acrylic acid-co-itaconic anhydride) are solved in 5 mL 1,4-dioxane. 0.6 g (4.6 mmol) HEMA and 10 mg butylated hydroxytoluene (BHT) are added and the solution is kept at 90° C. for 48 hours. After cooling down, the solution is concentrated to 2 mL on a rotary evaporator before the viscous liquid is precipitated in a 10-fold excess of acetonitrile. The obtained solid is stirred in 2 mL of water for 1 h and subsequently precipitated in acetonitrile and dried under reduced pressure. $^1$H-NMR (300 MHz, D$_2$O): δ [ppm]=12.5 (br, 10), 6.2 (br, 5), 5.7 (br, 6), 4.4 (br, 3 and 4), 2.8 (br, 2), 2.4 (br, 1 and 9), 1.8 (br, 8), 1.3 (br, 7).

Preparation of Aqueous Dental Glass Ionomer Compositions and Testing of Cured Compositions Aqueous dental glass ionomer compositions of Example 1 according to the disclosure and of the Comparative Examples 1 and 2 have been prepared by forming a liquid composition of the ingredients listed in Table 1 below, which add up to 100 wt %, and admixing the liquid composition with a reactive particulate glass powder in a powder/liquid ratio of 2.8/1.

The thus obtained dental glass ionomer compositions of Example 1 and Comparative Examples 1 and 2 were cured with a dental curing light. For the resulting cured dental glass ionomer composition, the flexural strength has been determined according to ISO 4049.

The invention claimed is:

1. An aqueous dental glass ionomer composition comprising
   (A) a reactive particulate glass,
   (B) a water-soluble, polymerizable polymer comprising acidic groups, which is reactive with the particulate glass in a cement reaction, whereby the polymerizable polymer has a polymer backbone and pendant groups having one or more polymerizable carbon-carbon double bonds, wherein the polymerizable polymer is obtained by a process comprising
      a) a step of polymerizing a mixture comprising
         (i) a first polymerizable monomer comprising at least one optionally protected carboxylic acid group and a first polymerizable organic moiety, and optionally
         (ii) a second copolymerizable monomer comprising one or more optionally protected primary and/or secondary hydroxyl and/or amino group(s) and a second polymerizable organic moiety,
      for obtaining a water-soluble polymer;
      b) a step of coupling to the water-soluble polymer a compound having a polymerizable moiety and a functional group reactive with an optionally protected carboxylic acid group of repeating units derived from the first polymerizable monomer or an optionally protected hydroxyl and/or amino group of repeating units derived from the second copolymerizable monomer in the water-soluble polymer obtained in step a), wherein the optionally protected carboxylic acid group and the optionally protected hydroxyl or amine group are deprotected, so that polymerizable pendant groups are linked to the backbone by ester groups, urethane groups and/or amide groups,
   and, optionally, a step of deprotecting the protected carboxylic acid group after step a) or step b), for obtaining a polymerizable polymer;
   (C) a hydrolysis-stable, water-soluble monomer having a single polymerizable double bond and optionally a carboxylic acid group or hydroxyl group; said monomer is a compound represented by the general formula (5):

TABLE 1

Liquid composition of the dental glass ionomer compositions of Example 1 and Comparative Examples 1 and 2, and flexural strength determined for the cured dental glass ionomer compositions

| Liquid composition of: | PAA-IAA-HEMA [wt %] | PAA-IAA [wt %] | AA [wt %] | HEAA [wt %] | HEMA [wt %] | BADEP [wt %] | water [wt %] | initiator/ inhibitor [wt %] | flexural strength [MPa] |
|---|---|---|---|---|---|---|---|---|---|
| Example 1 | 35.000 | 0.000 | 10.000 | 8.000 | 0.000 | 12.000 | 33.855 | 1.145 | 84 |
| Comparative Example 1 | 35.000 | 0.000 | 0.000 | 0.000 | 0.000 | 25.000 | 38.855 | 1.145 | 61 |
| Comparative Example 2 | 0.000 | 35.000 | 15.000 | 0.000 | 0.000 | 15.000 | 33.855 | 1.145 | 63 |

Legend of abbreviations:
PAA-IAA-HEMA poly(acrylic acid-co-itaconic anhydride) coupled with HEMA
PAA-IAA poly(acrylic acid-co-itaconic anhydride)
AA acrylic acid
HEAA 2-hydroxyethylacryl amide
HEMA 2-hydroxyethylmethacrylate
BADEP 1,3-bis(acrylamido)-N,N'-diethylpropane
initiator camphor quinone, dimethylamino benzontitrile
inhibitor tert.-butylhydroquinone

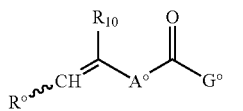

(5)

wherein $A^\circ$ is a single bond, or a linear $C_{1-6}$ or branched $C_{3-8}$ alkylene group which is bonded to the carbon-carbon double bond in formula (5) via a single bond or a carbonyl group (—CO—), wherein if the carbon number of the alkylene group is two or more, then the alkylene group may contain 1 to 3 heteroatoms, wherein each heteroatom is located in between two carbon atoms of the alkylene carbon chain, which heteroatoms are selected from an oxygen atom, nitrogen atom, and sulfur atom, and/or which alkylene group may contain, if its carbon number is two or more, in between two carbon atoms of the alkylene carbon chain 1 to 3 groups selected from an amide bond or a urethane bond;

$R^\circ$ is a hydrogen atom, a —COOZ group, or a linear $C_{1-6}$ or branched or cyclic $C_{3-8}$ alkyl group which may be substituted with a —COOZ group;

$R^{10}$ represents a hydrogen atom, —COOM, a linear $C_{1-18}$ or branched $C_{3-18}$ alkyl group which may be substituted with a $C_{3-6}$ cycloalkyl group, a $C_{6-14}$ aryl or $C_{3-14}$ heteroaryl group, —OM*, —COOM, —PO$_3$M, —O—PO$_3$M$_2$ or —SO$_3$M, a $C_3$ to $C_{18}$ cycloalkyl group which may be substituted with a $C_{1-16}$ alkyl group, a $C_{6-14}$ aryl or $C_{3-14}$ heteroaryl group, —OM*, —COOM, —PO$_3$M, —O—PO$_3$M$_2$ or —SO$_3$M, or a $C_5$ to $C_{18}$ aryl or $C_3$ to $C_{18}$ heteroaryl group which may be substituted with —OM*, —COOM, —PO$_3$M, —O—PO$_3$M$_2$ or —SO$_3$M, $G^\circ$ is —OH or a tertiary amino group —NR$_{11}$R*$_{11}$, wherein R$_{11}$ and R*$_{11}$ independently represent a hydrogen atom, a linear $C_{1-18}$ or branched $C_{3-18}$ alkyl group which may be substituted with a $C_{3-6}$ cycloalkyl group, a $C_{6-14}$ aryl or $C_{3-14}$ heteroaryl group, —OM*, —COOM, —PO$_3$M, —O—PO$_3$M$_2$ or —SO$_3$M, a $C_{3-18}$ cycloalkyl group which may be substituted with a $C_{1-16}$ alkyl group, a $C_{6-14}$ aryl or $C_{3-14}$ heteroaryl group, —OM*, —COOM, —PO$_3$M, —O—PO$_3$M$_2$ or —SO$_3$M, or a $C_{5-18}$ aryl or $C_{3-18}$ heteroaryl group which may be substituted with —OM*, —COOM, —PO$_3$M, —O—PO$_3$M$_2$ or —SO$_3$M, wherein R$_{11}$ and R*$_{11}$ may cooperatively form a ring in which R$_{11}$ and R*$_{11}$ may be linked by a C—C bond or a functional group which may be selected from the group consisting of an ether group, a thioether group, an amine group and an amide group, with the proviso that R$_{11}$ and R*$_{11}$ cannot both be a hydrogen atom, m is an integer in a range from 1 to 10, M* of any one R$_{10}$, R$_{11}$ and R*$_{11}$, which M* are independent from each other, each represent a hydrogen atom or a hydroxyl-protecting group, and M of any one R$_{10}$, R$_{11}$ and R*$_{11}$, which M are independent from each other, each represent a hydrogen atom, a carboxyl-protecting group or a metal atom; and (D) a polymerization initiator system;

wherein the hydrolysis-stable, water-soluble monomer according to (C) does not contain an ester group.

2. The aqueous dental glass ionomer composition according to claim 1, further comprising at least one of the following features:

the aqueous dental glass ionomer composition does not comprise a non-polymerizable polymer having no polymerizable carbon-carbon double bond(s);

the hydrolysis-stable, water-soluble monomer according to (C) has a molecular weight of at most 600 Da.

3. The aqueous dental glass ionomer composition according to claim 1, further comprising at least one of the following features:

the hydrolysis-stable, water-soluble monomer according to (C) is contained in an amount of from 1 to 10 percent by weight based on the total weight of the aqueous dental glass ionomer composition;

the aqueous dental glass ionomer composition according to claim 1, which further comprises (E) a non-reactive filler;

the aqueous dental glass ionomer composition according to claim 1, wherein the molar ratio of first polymerizable monomer to second copolymerizable monomer in the mixture copolymerized in step a) (mol first polymerizable monomer/mol second copolymerizable monomer) is in the range of from 100:1 to 100:50.

4. The aqueous dental glass ionomer composition according to claim 1, wherein the first polymerizable monomer is represented by a general formula (1):

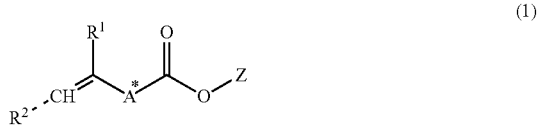

(1)

wherein $R^1$ is a hydrogen atom, a —COOZ group, a linear $C_{1-6}$ or branched or cyclic $C_{3-8}$ alkyl group which may be substituted with a —COOZ group, or a $C_{6-10}$ aryl group which may be substituted with a —COOZ group;

$R^2$ is a hydrogen atom, a —COOZ group, or a linear $C_{1-6}$ or branched or cyclic $C_{3-8}$ alkyl group which may be substituted with a —COOZ group;

A* is a single bond, or a linear $C_{1-6}$ or branched or cyclic $C_{3-8}$ alkylene group, wherein if the carbon number of the alkylene group is two or more, then the alkylene group may contain 1 to 3 heteroatoms, wherein each heteroatom is located in between two carbon atoms of the alkylene carbon chain, which heteroatoms are selected from an oxygen atom, nitrogen atom, and sulfur atom, and/or which alkylene group may contain, if its carbon number is two or more, in between two carbon atoms of the alkylene carbon chain 1 to 3 groups selected from an amide bond or a urethane bond;

Z which may be the same or different, independently represents a hydrogen atom, a metal ion, a protecting group for a carboxylic acid group, or the Z forms with a further —COOZ group present in the molecule an intramolecular anhydride group.

5. The aqueous dental glass ionomer composition according to claim 1, wherein the second copolymerizable monomer is represented by a general formula (2):

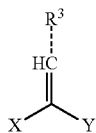
(2)

wherein

R³ is a hydrogen atom, or a linear $C_{1-6}$ or branched or cyclic $C_{3-6}$ alkyl group which may be substituted with a —COOZ' group;

X is a protected hydroxyl or amino group, or a hydrocarbon group having 1 to 20 carbon atoms, which is substituted with a hydroxyl and/or amino group which may carry a protecting group, wherein the hydrocarbon group may contain 1 to 6 heteroatoms, which heteroatoms are selected from an oxygen atom, nitrogen atom, and sulfur atom, and/or which hydrocarbon group may contain a group selected from an amide bond or a urethane bond and which hydrocarbon group may further be substituted with up to 6 groups selected from —COOZ', amino groups and thiol groups;

Y is a hydrogen atom, a —COOZ' group, or a hydrocarbon group having 1 to 20 carbon atoms, wherein the hydrocarbon group may contain 1 to 6 heteroatoms, which heteroatoms are selected from an oxygen atom, nitrogen atom, and sulfur atom, and/or which hydrocarbon group may contain a group selected from an amide bond or a urethane bond and which hydrocarbon group may further be substituted with up to 6 groups selected from —COOZ', amino groups, hydroxyl groups and thiol groups;

Z' which may be the same or different, independently represents a hydrogen atom, a metal ion, a protecting group for a carboxylic acid group, or the Z' forms with a further —COOZ' group present in the molecule an intramolecular anhydride group.

6. The aqueous dental glass ionomer composition according to claim 1, wherein the compound having a polymerizable moiety and a functional group reactive with an optionally protected carboxylic acid group of repeating units derived from the first copolymerizable monomer is a compound represented by a general formula (3):

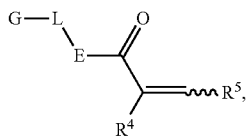
(3)

wherein

G is a hydroxyl group or an amino group, which group may carry a protecting group;

E is an oxygen atom or a secondary amino group (NH) or a tertiary amino group NR# wherein R# is a linear $C_{1-6}$ or branched or cyclic $C_{3-8}$ alkyl group;

R⁴ is a hydrogen atom, or a linear $C_{1-6}$ or branched or cyclic $C_{3-8}$ alkyl group which may be substituted with a —COOZ" group;

R⁵ is a hydrogen atom, or a linear or branched or cyclic $C_{3-8}$ alkyl group which may be substituted with a —COOZ" group;

Z" which may be same or different, independently represents a hydrogen atom, a metal ion, a protecting group for a carboxylic acid group, or the Z" forms with a further —COOZ" group present in the molecule an intramolecular anhydride group;

L is a linear $C_{1-6}$ or branched or cyclic $C_{3-8}$ alkylene group, wherein if the carbon number of the alkylene group is two or more, then the alkylene group may contain 1 to 3 heteroatoms, wherein each heteroatom is located in between two carbon atoms of the alkylene carbon chain, which heteroatoms are selected from an oxygen atom, nitrogen atom, and sulfur atom, and/or which alkylene group may contain, if its carbon number is two or more, in between two carbon atoms of the alkylene carbon chain 1 to 3 groups selected from an amide bond or a urethane bond.

7. The aqueous dental glass ionomer composition according to claim 1, wherein the compound having a polymerizable moiety and a functional group reactive with an optionally protected hydroxyl and/or amino group of repeating units derived from the second copolymerizable monomer is a compound represented by a general formula (4):

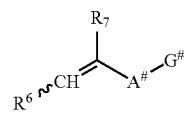
(4)

wherein

G# is —N=C=O or —CO-LG wherein LG is a leaving group or wherein
LG may replace Z''' and form with R⁶ or R⁷ an intramolecular carboxylic acid anhydride group, or wherein two molecules of formula (4) form an intermolecular carboxylic acid anhydride group by condensation of LG and/or —COOZ''', wherein LG is an oxygen atom;

A# is a single bond, or a linear $C_{1-6}$ or branched or cyclic $C_{3-8}$ alkylene group which is bonded to the carbon-carbon bond of formula (4) via a single bond or a carbonyl group (—CO—), wherein if the carbon number of the alkylene group is two or more, then the alkylene group may contain 1 to 3 heteroatoms, wherein each heteroatom is located in between two carbon atoms of the alkylene carbon chain, which heteroatoms are selected from an oxygen atom, nitrogen atom, and sulfur atom, and/or which alkylene group may contain, if its carbon number is two or more, in between two carbon atoms of the alkylene carbon chain 1 to 3 groups selected from an amide bond or a urethane bond;

R⁶ is a hydrogen atom, a —COOZ''' group, or a linear $C_{1-6}$ or branched or cyclic $C_{3-8}$ alkyl group which may be substituted with a —COOZ''' group;

R⁷ is a hydrogen atom, a —COOZ''' group, or a linear $C_{1-6}$ or branched or cyclic $C_{3-8}$ alkyl group which may be substituted with a —COOZ''' group;

Z''' which may be same or different, independently represents a hydrogen atom, a metal ion, a protecting group for a carboxylic acid group, or the Z''' forms with a further —COOZ''' group present in the molecule an intramolecular anhydride group.

8. The aqueous dental glass ionomer composition according to claim 1, wherein the hydrolysis-stable, water-soluble monomer is a (meth)acrylamide monomer represented by a general formula (5''')

wherein $R_{10}''$ represents a hydrogen atom, a linear $C_{1-6}$ or branched or cyclic $C_{3-8}$ alkyl group which may be substituted with a cyclohexyl group or a phenyl group, or a $C_{4-8}$ cycloalkyl group which may be substituted with a $C_{1-4}$ alkyl group, $R_{11}''$ and $R^*_{11}''$ independently represent a hydrogen atom, a linear $C_{1-10}$ or branched $C_{3-10}$ alkyl group which may be substituted with a $C_{6-10}$ aryl group or —OH, a cyclic $C_{3-10}$ alkyl group which may be substituted with —OH, or $R_{11}''$ and $R^*_{11}''$ independently represent a linear $C_{1-10}$ or branched $C_{3-10}$ alkyl group which cooperatively form a ring in which $R_{11}''$ and $R^*_{11}''$ are linked by a C—C bond or an ether group, with the proviso that $R_{11}''$ and $R^*_{11}''$ cannot both be a hydrogen atom.

9. The aqueous dental glass ionomer composition according to claim 1, further comprising at least one of the following features:
   in step a) of (B), the obtained water-soluble polymer does not comprise a pendant ß-dicarbonyl group
   in step b) of (B), the water-soluble polymer is reacted with compound of formula (3) wherein G is a hydroxyl group;
   in step a) of (B), in the water-soluble polymer obtained, all carboxylic acid groups are protected, which water-soluble polymer is reacted in step b) of (B) with the compound of formula (4).

10. The aqueous dental glass ionomer composition according to claim 1, further comprising at least one of the following features:
    the polymerizable polymer comprising acidic groups has a molecular weight $M_w$ in the range of from $10^3$ to $10^6$ Da;
    the particulate glass comprises
    1) 20 to 45% by weight of silica,
    2) 20 to 40% by weight of alumina,
    3) 20 to 40% by weight of strontium oxide,
    4) 1 to 10% by weight of $P_2O_5$, and
    5) 3 to 25% by weight of fluoride
    aqueous dental glass ionomer composition comprises 20 to 80 percent by weight of the reactive particulate glass, based on the total weight of the composition and/or comprises 10 to 80 percent by weight of the polymer comprising acidic groups, based on the total weight of the composition, and/or comprises up to 75 percent by weight of dispersed nanoparticles based on the total weight of the composition;
    the aqueous dental glass ionomer composition, which, when cured, has an adhesive bond strength to dentin of at least 5 MPa as measured according to ISO 29022: 2013; and/or
    a flexural strength of at least 50 MPa as measured according to ISO 4049.

11. A dental composition comprising an aqueous dental glass ionomer composition, wherein the aqueous dental glass ionomer composition includes:
    (A) a water-soluble, polymerizable polymer comprising acidic groups, which is reactive with the particulate glass in a cement reaction, whereby the polymerizable polymer has a polymer backbone and pendant groups having one or more polymerizable carbon-carbon double bonds, wherein the polymerizable polymer is obtained by a process comprising
    a) a step of polymerizing a mixture comprising
       (i) a first polymerizable monomer comprising at least one optionally protected carboxylic acid group and a first polymerizable organic moiety, and
       (ii) optionally copolymerizing a second copolymerizable monomer comprising one or more optionally protected primary and/or secondary hydroxyl and/or amino group(s) and a second polymerizable organic moiety, for obtaining an water-soluble polymer;
    b) a step of coupling to the water-soluble polymer a compound having a polymerizable moiety and a functional group reactive with an optionally protected carboxylic acid group of repeating units derived from the first polymerizable monomer or an optionally protected hydroxyl and/or amino group of repeating units derived from the second copolymerizable monomer in the water-soluble polymer obtained in step a), wherein the optionally protected carboxylic acid group and the optionally protected hydroxyl and/or amine group are deprotected, so that polymerizable pendant groups are linked to the backbone by ester groups or urethane groups and/or amide groups,
    and, optionally, a step of deprotecting the protected carboxylic acid group after step a) or step b), for obtaining a polymerizable polymer;
    and
    (B) a hydrolysis-stable, water-soluble monomer having a single polymerizable double bond and optionally a carboxylic acid group or hydroxyl group; said monomer is a compound represented by the general formula (5):

wherein $A^○$ is a single bond, or a linear $C_{1-6}$ or branched $C_{3-8}$ alkylene group which is bonded to the carbon-carbon double bond in formula (5) via a single bond or a carbonyl group (—CO—), wherein if the carbon number of the alkylene group is two or more, then the alkylene group may contain 1 to 3 heteroatoms, wherein each heteroatom is located in between two carbon atoms of the alkylene carbon chain, which heteroatoms are selected from an oxygen atom, nitrogen atom, and sulfur atom, and/or which alkylene group may contain, if its carbon number is two or more, in between two carbon atoms of the alkylene carbon chain 1 to 3 groups selected from an amide bond or a urethane bond;

$R^○$ is a hydrogen atom, a —COOZ group, or a linear $C_{1-6}$ or branched or cyclic $C_{3-8}$ alkyl group which may be substituted with a —COOZ group;

$R^{10}$ represents a hydrogen atom, —COOM, a linear $C_{1-18}$ or branched $C_{3-18}$ alkyl group which may be substituted with a $C_{3-6}$ cycloalkyl group, a $C_{6-14}$ aryl or $C_{3-14}$ heteroaryl group, —OM*, —COOM, —$PO_3M$, —O—$PO_3M_2$ or —$SO_3M$, a $C_3$ to $C_{18}$ cycloalkyl group which may be substituted with a $C_{1-16}$ alkyl group, a $C_{6-14}$ aryl or $C_{3-14}$ heteroaryl group, —OM*, —COOM, —$PO_3M$, —O—$PO_3M_2$ or —$SO_3M$, or a $C_5$ to $C_{18}$ aryl or $C_3$ to $C_{18}$ heteroaryl group which may be substituted with —OM*, —COOM, —$PO_3M$, —O—$PO_3M_2$ or —$SO_3M$, $G^{\ominus}$ is —OH or a tertiary amino group —$NR_{11}R^*_{11}$, wherein $R_{11}$ and $R^*_{11}$ independently represent a hydrogen atom, a linear $C_{1-18}$ or branched $C_{3-18}$ alkyl group which may be substituted with a $C_{3-6}$ cycloalkyl group, a $C_{6-14}$ aryl or $C_{3-14}$ heteroaryl group, —OM*, —COOM, —$PO_3M$, —O—$PO_3M_2$ or —$SO_3M$, a $C_{3-18}$ cycloalkyl group which may be substituted with a $C_{1-16}$ alkyl group, a $C_{6-14}$ aryl or $C_{3-14}$ heteroaryl group, —OM*, —COOM, —$PO_3M$, —O—$PO_3M_2$ or —$SO_3M$, or a $C_{5-18}$ aryl or $C_{3-18}$ heteroaryl group which may be substituted with —OM*, —COOM, —$PO_3M$, —O—$PO_3M_2$ or —$SO_3M$, wherein $R_{11}$ and $R^*_{11}$ may cooperatively form a ring in which $R_{11}$ and $R^*_{11}$ may be linked by a C—C bond or a functional group which may be selected from the group consisting of an ether group, a thioether group, an amine group and an amide group, with the proviso that $R_{11}$ and $R^*_{11}$ cannot both be a hydrogen atom, m is an integer in a range from 1 to 10, M* of any one $R_{10}$, $R_{11}$ and $R^*_{11}$, which M* are independent from each other, each represent a hydrogen atom or a hydroxyl-protecting group, and M of any one $R_{10}$, $R_{11}$ and $R^*_{11}$, which M are independent from each other, each represent a hydrogen atom, a carboxyl-protecting group or a metal atom;

wherein the hydrolysis-stable, water-soluble monomer does not contain an ester group.

12. A process for the preparation an aqueous dental glass ionomer composition as recited in claim 1, the process comprising:

a) a step of polymerizing a mixture comprising
(i) a first polymerizable monomer comprising at least one optionally protected carboxylic acid group and a first polymerizable organic moiety, and optionally
(ii) a second copolymerizable monomer comprising one or more optionally protected primary and/or secondary hydroxyl and/or amino group(s) and a second polymerizable organic moiety, for obtaining a water-soluble polymer;

b) a step of coupling to the water-soluble polymer a compound having a polymerizable moiety and a functional group reactive with an optionally protected carboxylic acid group of repeating units derived from the first polymerizable monomer or an optionally protected hydroxyl and/or amino group of repeating units derived from the second copolymerizable monomer in the water-soluble polymer obtained in step a), wherein the optionally protected carboxylic acid group and the optionally protected hydroxyl or amine group are deprotected, so that polymerizable pendant groups are linked to the backbone by ester groups, urethane groups and/or amide groups, and, optionally, a step of deprotecting the protected carboxylic acid group after step a) or step b), for obtaining a polymerizable polymer.

13. The process according to claim 12, further comprising at least one of the following features:
the water-soluble polymer is selected from a polyacid and a polyanhydride;
the step b) of coupling to the water-soluble polymer comprises activation of the water-soluble polymer;
the water-soluble polymer is a cyclopolymer.

14. The process according to claim 12, wherein in step b), the functional group reactive with an optionally protected carboxylic acid group of repeating units derived from the first polymerizable monomer in the water-soluble polymer obtained in step a) is a group —OR' wherein R' is a hydrogen atom, or a linear $C_{1-6}$ or branched $C_{3-8}$ alkyl group, and/or the functional group reactive with an optionally protected hydroxyl and/or amino group of repeating units derived from the second copolymerizable monomer in the water-soluble polymer obtained in step a) is an isocyanate group or a —CO-LG' group wherein LG' denotes a leaving group being a chlorine atom, a bromine atom, or forms with the adjacent carbonyl group a carboxylic acid anhydride moiety.

15. The aqueous dental glass ionomer composition according to claim 8, wherein the compound of formula (5''') is selected from the group consisting of

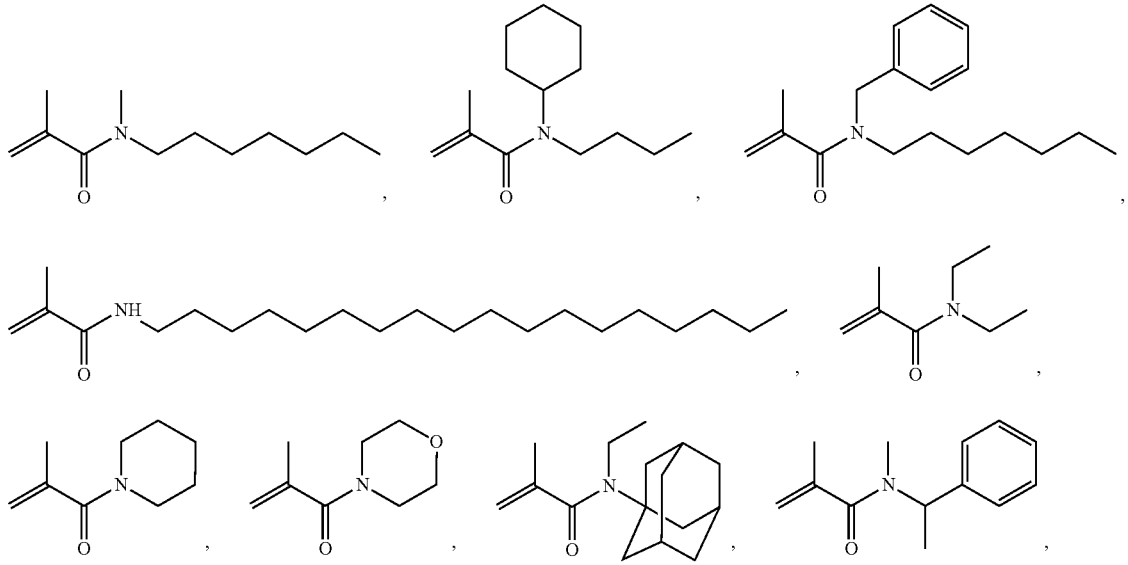

-continued
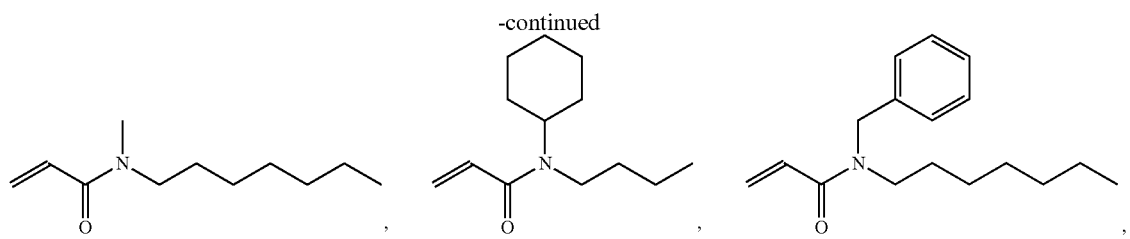
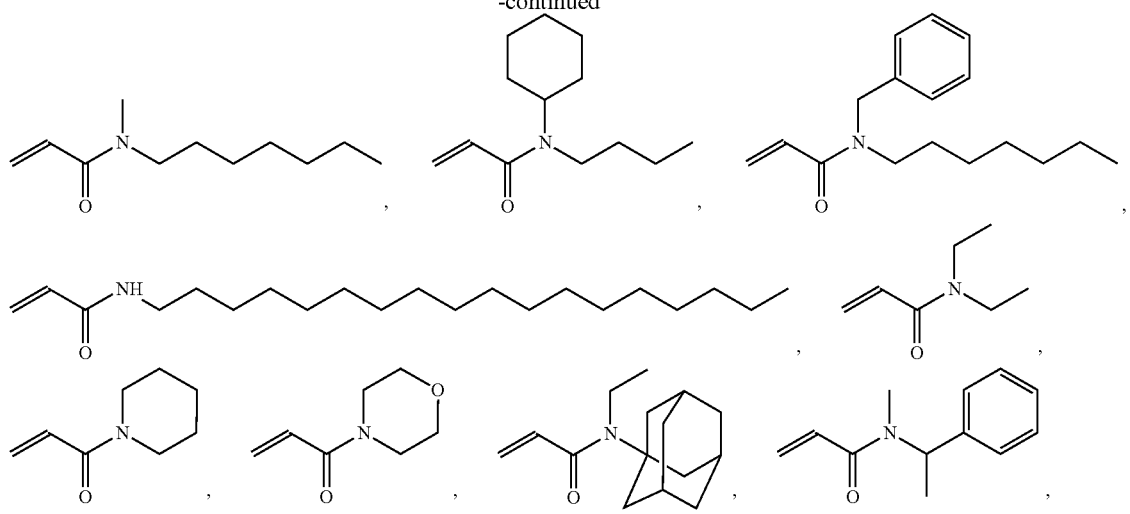
2-hydroxyethyl acrylamide (HEAA), N,N-dimethyl(meth)acrylamide, N,N-di-n-propyl(meth)acrylamide, and N-ethyl-N-methyl(meth)acrylamide.
* * * * *